United States Patent
Ricciardelli et al.

(10) Patent No.: US 8,459,261 B2
(45) Date of Patent: Jun. 11, 2013

(54) SIDE-STREAM RESPIRATORY GAS MONITORING SYSTEM AND METHOD

(75) Inventors: Robert H. Ricciardelli, Waukesha, WI (US); Michael J. Marking, Menomonee Falls, WI (US)

(73) Assignee: Treymed, Inc., Sussex, WI (US)

( * ) Notice: Subject to any disclaimer, the term of this patent is extended or adjusted under 35 U.S.C. 154(b) by 573 days.

(21) Appl. No.: 11/560,462

(22) Filed: Nov. 16, 2006

(65) Prior Publication Data

US 2007/0107728 A1   May 17, 2007

Related U.S. Application Data

(60) Provisional application No. 60/737,231, filed on Nov. 16, 2005.

(51) Int. Cl.
*A61M 16/00* (2006.01)
*A62B 7/00* (2006.01)
*A62B 9/00* (2006.01)

(52) U.S. Cl.
USPC ............ 128/204.23; 128/204.18; 128/205.23; 128/200.24

(58) Field of Classification Search
USPC ............ 128/200.24, 203.12, 203.17, 203.26, 128/203.27, 204.18, 204.21, 204.23; 600/504, 600/486, 526, 529, 532, 538; 73/23.2; 422/84; 702/45, 53, 66, 67, 100, 104, 189
See application file for complete search history.

(56) References Cited

U.S. PATENT DOCUMENTS

| | | | |
|---|---|---|---|
| 4,463,764 A * | 8/1984 | Anderson et al. ............. | 600/532 |
| 4,680,956 A | 7/1987 | Huszczuk | |
| 4,687,934 A * | 8/1987 | Passaro et al. ............... | 250/343 |
| 5,038,773 A | 8/1991 | Norlien et al. | |
| 5,092,342 A | 3/1992 | Hattendorff et al. | |
| 5,146,092 A | 9/1992 | Apperson et al. | |
| 5,233,996 A | 8/1993 | Coleman et al. | |
| 5,398,676 A * | 3/1995 | Press et al. ............... | 128/204.23 |
| 5,398,695 A | 3/1995 | Anderson et al. | |
| 5,429,123 A * | 7/1995 | Shaffer et al. ............ | 128/204.23 |
| 5,590,644 A | 1/1997 | Rosenkoetter | |
| 5,611,348 A * | 3/1997 | Merilainen ................... | 600/543 |
| 5,676,131 A | 10/1997 | Anderson et al. | |
| 5,689,203 A * | 11/1997 | Geist ............................ | 327/187 |
| 5,705,735 A | 1/1998 | Acorn | |
| 5,827,179 A | 10/1998 | Lichter et al. | |

(Continued)

OTHER PUBLICATIONS

Roger Fletcher, *The Single Breath Test for Carbon Dioxide*, Departments of Anaesthesia and Clinical Physiology, University of Lund, Lund, Sweden 1986.

*Primary Examiner* — Annette Dixon
(74) *Attorney, Agent, or Firm* — Boyle Fredrickson, S.C.

(57) ABSTRACT

A side-stream respiration monitoring system includes a sensor, a monitor, and a display. The sensor is constructed to engage respiration flows having a variable flow amounts and acquire a respiration sample from the flow. The monitor is connected to the sensor and configured to determine the amount of respiration flow as well as the amount of several constituents of the respiration flow such as oxygen, carbon dioxide, water, and nitrous oxide. The monitor is also configured to adjust the determined values for ambient environment variations and is self-calibrating with respect to the ambient conditions. The monitor temporally aligns the acquired data to account for dead-space respiration events and physiological respiration modifications such as cardiac events. Information generated by the monitor is communicated to an operator via a display configured to display the real-time respiration performance.

76 Claims, 22 Drawing Sheets

U.S. PATENT DOCUMENTS

| | | |
|---|---|---|
| 5,925,831 A | 7/1999 | Storsved |
| D413,825 S | 9/1999 | Storsved |
| 5,997,483 A | 12/1999 | Johnson |
| 6,044,843 A | 4/2000 | O'Neil et al. |
| 6,113,549 A | 9/2000 | Johnson |
| 6,131,571 A * | 10/2000 | Lampotang et al. ..... 128/204.21 |
| 6,159,147 A | 12/2000 | Lichter et al. |
| 6,258,040 B1 | 7/2001 | Yamamori et al. |
| 6,305,212 B1 * | 10/2001 | Drzewiecki .................... 73/23.2 |
| 6,571,200 B1 | 5/2003 | Mault |
| 6,572,561 B2 | 6/2003 | Mault |
| 6,585,661 B1 | 7/2003 | Hunt et al. |
| 6,607,387 B2 | 8/2003 | Mault |
| 6,609,016 B1 * | 8/2003 | Lynn ............................ 600/323 |
| 6,616,615 B2 | 9/2003 | Mault |
| 6,620,106 B2 | 9/2003 | Mault |
| 6,629,934 B2 | 10/2003 | Mault et al. |
| 6,632,402 B2 | 10/2003 | Blazewicz et al. |
| 6,645,158 B2 | 11/2003 | Mault |
| 6,802,225 B2 | 10/2004 | Shahar et al. |
| 6,938,619 B1 * | 9/2005 | Hickle .................... 128/207.18 |
| 6,969,357 B1 | 11/2005 | Colman et al. |
| 7,121,134 B2 | 10/2006 | Rich |
| 7,152,604 B2 * | 12/2006 | Hickle et al. ............. 128/207.14 |
| 7,201,734 B2 * | 4/2007 | Hickle ............................ 604/67 |
| 7,556,039 B1 * | 7/2009 | Pierry ...................... 128/204.22 |
| 2004/0127808 A1 | 7/2004 | Vaughan et al. |
| 2004/0162500 A1 | 8/2004 | Kline |
| 2004/0254491 A1 | 12/2004 | Ricciardelli |

* cited by examiner

SIDE-STREAM RESPIRATORY GAS MONITORING SYSTEM AND METHOD

CROSS REFERENCE TO RELATED APPLICATIONS

This application is a non-provisional application and claims priority to Provisional Patent Application Ser. No. 60/737,231, filed on Nov. 16, 2005 titled Side-Stream Respiratory Gas Monitoring System and Method, the disclosure of which is incorporated herein.

FIELD OF THE INVENTION

The present invention relates to a system and method for monitoring respiration and, more particularly to a side-stream monitoring system configured to monitor respiratory and physiological performance of a person being monitored. The invention provides a system and method for real time, breadth-by-breadth side-stream monitoring of a patient. The system monitors respiration flow rate and flow constituents to assess various parameters of a patient's physiological condition and respiration performance.

BACKGROUND OF THE INVENTION

It is generally well accepted that monitoring respiration performance provides diagnostic insight into a patient's overall health as well as specific respiratory function. Understandably, the accuracy of any diagnosis or conclusion based on respiratory performance depends upon the skill of the technician interpreting the interpretation as well, the accuracy of the information acquired, and the timeliness of the calculation of the information. Respiratory monitoring generally requires the acquisition of the breath sample and a determination of a make-up or composition of the acquired breath sample. Physiologic events, patient condition, equipment construction and operation, and ambient conditions directly affect the accuracy of the information acquired by the respiration monitoring system. Accordingly, failure to account for activities associates with these events detrimentally affects the accuracy of the information acquired and any conclusions based thereon. Furthermore, the timeliness of the respiration performance determination directly affects patient treatment determinations.

The cardiac cycle is one physiological event that can be taken into account in generating respiratory performance information. During the cardiac cycle, expansion of the chambers of the heart compresses against the lungs and generates a flow anomaly in the respiration cycle. Although the flow anomaly is internally imperceptible to most people, the flow anomaly presents a discontinuity in the respiratory flow that, if unaddressed, can lead to inaccurate interpretation of respiration performance. Other physiological conditions, such as poor lung performance, can also detrimentally affect interpretation of monitored respiration information. Flow path dead-space is another factor that must be addressed to provide an accurate determination of respiration performance. The flow path dead-spaces include patient respiration dead-spaces as well as dead-spaces associated with respiration monitoring system, or aspiration dead-spaces.

Respiration flow path dead-spaces are those portions of a respiration path that are susceptible to retaining exhalation or inhalation gases. Within a patient, the tracheal passage, mouth, and tongue can each contribute to respiration flow dead-spaces. Gases from a previous inhalation or exhalation cycle may momentarily remain in these spaces even though a subsequent inhalation or exhalation has begun. Within the monitoring equipment, the connection lines and sensor construction can each present dead-space data collection errors. That is, the lines that connect the sensor to the monitor and the sensor inserted into the respiration flow path may each retain gases associated with a previous inhalation of exhalation cycle. The accuracy of any respiration monitoring depends in part upon the monitoring systems ability to correct the respiration performance information for each of these exemplary dead-spaces.

Ambient conditions also affect the accuracy of the information acquired during respiration monitoring. For example, in an oxygen rich environment, an exhalation that includes elevated levels of oxygen would not provide an accurate indication of respiration performance if compared to respiration performance for an environment that does not include the elevated levels of oxygen. Similarly, an exhalation that includes excessive amounts of carbon dioxide provides no indication of the physiological performance if the testing environment is already rich in carbon dioxide. Accordingly, accurate respiration monitoring system must also account for deviations in the ambient test conditions.

Capnography, or the measurement of carbon dioxide in an exhalation, is commonly performed in many medical fields, including ventilated patients. Knowing the concentration of carbon dioxide as a function of time renders information about breath frequency, e.g. breaths per minute, and inspired or re-breathed levels of carbon dioxide. In some circumstances there is good agreement between the highest levels measured, often the end-tidal concentration of the carbon dioxide, and an arterial concentration, which is of value in caring for seriously compromised individuals. Understandably, such methods of comparing exhaled carbon dioxide levels to arterial carbon dioxide levels lack real-time monitoring of respiration performance.

Ascertaining an actual amount of a chemical being consumed or generated by a patient enhances the temporal or real-time monitoring and diagnosis of a patient condition. That is, monitoring both the respiration composition as well as volume enhances the diagnostic feature of a respiration monitoring system. Prior methods have relied upon collecting the exhalation gases and analyzing them sometime after the exhalation to ascertain the condition of the patient. This method, commonly referred to as the "Douglas Bag" collection method, is cumbersome, labor intensive, and discounts all of the information that can be acquired with real-time breath-by-breath data acquisition and analysis. This method is also commonly referred to as 'indirect calorimetry' for its indirect determination of the caloric expenditure of a patient by quantifying the carbon dioxide produced. Accordingly, it is desired to provide a respiration monitoring system that is configured to directly measure gas volumes as they are being produced or in real-time and preferably on a breath-by-breath basis.

To accomplish the measuring of gas volumes on a breath-by-breath basis, the gas concentrations as a function of time must be collected simultaneously with the flow information. Gas concentrations measured at the same location and at the same time as the flow measurement are commonly referred to as mainstream monitoring. A disadvantage of mainstream monitoring is that the monitoring is commonly performed at the location of the patient's exhaled breadth, i.e., the mouth, or as close to the site of exhalation as possible. The equipment commonly utilized for such monitoring generally tends to be large, cumbersome, and costly. Another drawback of such monitoring systems is the increase in dead-space volumes that must be overcome by a patient. Attempts at miniaturizing these devices only further increases the cost associated with these diagnostic tools. Accordingly, there is a need for a lightweight, portable respiration monitoring system with reduced dead-space volumes.

Although side-stream systems, also known as metabolic carts, address most of these issues, such systems present other drawbacks. A side-stream system draws a sample of the patient's breath and transmits it to a remote gas concentration analyzer. A side-stream system is normally capable of measuring the flow in real time. However, the acquired expiration sample must travel some distance thru lumen tubing or the like to reach the gas content analyzer. Since the gas sample is analyzed at some time after the passage of the patients flow, such side-stream systems present a temporal misalignment between the value of the respiration flow and the gas concentration values. This temporal or time wise misalignment makes side-stream systems more difficult to implement and the data acquired therefrom more difficult to interpret. Accordingly, technicians must be extensively trained in the operation and understanding of the information acquired with such systems. As such, there is also a need for a respiration monitoring system that is cost effective to manufacture, implement, and operate.

Another consideration of respiration monitoring systems is calibration of the monitoring system as well as the display of the acquired information. The calibration of known respiratory monitoring systems is a time consuming and labor intensive process. The calibration generally consists of a technician passing a known volume of a known gas several times into the monitoring system. The combination of the known gas and the relatively known volume provides operative information that provides for calibrating the monitoring system. Unfortunately, the calibration process is generally only performed at the initiation of a monitoring session, must be frequently repeated to ensure the accurate operation of the monitoring system, and does not adequately address variations in the testing environment. Additionally, such calibration generally relies heavily on the experience of the technician performing the calibration and the availability of the calibration tools such as a gas tube injector of a known volume and a known gas.

The output of known monitoring systems also presents the potential for misinterpretation. During inhalation, the monitored oxygen level should be at a maximum level and the monitored carbon dioxide level should be at a minimum, i.e. ambient conditions. During exhalation, the detected oxygen level should be at a minimum and the detected carbon dioxide level should be a maximum. The inverse relationship of the oxygen level and the carbon dioxide level across a respiration cycle as well as the dynamic function of the respiration flow is generally not temporary aligned across a respiration cycle. As shown in FIG. 1, the respiration information is generally produced with no cyclic alignment and a technician must mentally align the output to generate a real-time flow and composition of the respiratory function. FIG. 1 represents a trend plot 8 that includes a carbon dioxide trend 10 and a flow trend 12. A first ordinate 14 shows that the carbon dioxide trend 10 is always positive as indicated by abscissa 15 and ranges from a plurality of relative minimums 16 to a plurality of relative maximums 18. As discussed above, the relative maximums 18 of the carbon dioxide trend 10 reflect patient expiration whereas areas proximate relative minimums 16 reflect carbon dioxide levels associated with dead-space data acquisition and ambient carbon dioxide levels.

Flow trend 12 is indexed at second ordinate 20. Flow trend 12 repeatedly crosses abscissa 15 such that positive values indicate an inhalation and negative values indicate an exhalation. As discussed above, each exhalation, a flow associated with a negative flow trend value, should correlate to a relative maximum of the carbon dioxide trend. As indicated with the reference letters A, B, C, and D, temporally aligning the flow trend and the carbon dioxide trend requires phase shifting of flow trend 12 to the right relative to carbon dioxide trend 10. An identifier must be acquired to ensure an appropriate shift of the relative trends in determine the time-wise alignment of the flow and respiration composition information. Another lacking of known respiration monitoring systems is the ability to concurrently align a respiration flow value, a carbon dioxide concentration value, and an oxygen concentration value. Frequently, a carbon dioxide value and an oxygen value are displayed on different axis or completely different screens and therefore are not time aligned for interpretation.

Each of the drawbacks discussed above result in shortcomings in the implementation of known respiration monitoring systems. The cost and complexity of these respiration monitoring systems result in their infrequent utilization or improper interpretation of the results acquired with such systems. Furthermore, the information acquired and utilized by such systems limits the diagnostic functionality of such systems in disregarding that information that can be utilized by time aligning the variable functions of the respiration cycle and variations in operation of the monitoring system.

Accordingly, there is a need for a real-time respiratory monitoring system that is configured to align respiration flow information and respiration composition information. Furthermore, there is a need for a respiration monitoring system that is simple and efficient to manufacture and operate and one which provides concise real-time time aligned respiration information.

BRIEF DESCRIPTION OF THE INVENTION

The present invention is directed to a respiration monitoring system that overcomes the aforementioned drawbacks. The monitoring system includes a sensor, a monitor, and a display. The sensor is constructed to engage respiration flows having variable flow amounts and acquire a respiration sample from the flow. The monitor is connected to the sensor and configured to determine the amount of respiration flow as well as the amount of several constituents of the respiration flow such as oxygen, carbon dioxide, water, and nitrous oxide. The monitor is also configured to adjust the determined values for ambient condition variations and is self-calibrating with respect to the ambient conditions and operation of the monitoring system. The monitor temporally aligns the determined data to account for dead-space respiration events and physiological respiration variants such as cardiac events. Information generated by the monitor is communicated to an operator via a display configured to display the real-time respiration performance such that the measured parameters are time aligned with the other respiration cycle information.

One aspect of the disclosed invention includes a side-stream respiration monitoring system having a flow sensor and a controller. The flow sensor is constructed to be disposed in a respiration flow path to detect various parameters of the respiration flow. The controller is connected to the flow sensor and is configured to determine a respiration flow value and at least a portion of a composition of the flow. The controller temporally associates the respiration flow value and the portion of the composition on an approximately breath-by-breath basis to provide real-time breath-by-breath respiration monitoring.

Another aspect of the invention includes a respiration monitoring system that has a flow sensor, an analyzer, and a controller. The sensor is constructed to detect a respiration flow and acquire a side-stream sample of the flow. The analyzer is constructed to determine an amount of a gas carried on the respiration flow and the controller is configured to automatically calibrate the analyzer.

A side-flow respiration monitoring system according to another aspect of the invention includes a sensor for detecting a respiration flow and acquiring a sample of the respiration flow. A monitor is connected to the sensor for determining an amount of oxygen and an amount of carbon dioxide in the respiration flow on a breath-by-breath basis. A display is connected to the monitor for displaying information associated with the amount of oxygen and carbon dioxide on a common plot to provide comprehensive time-aligned respiration information.

A further aspect of the invention discloses a method of monitoring respiration information that includes measuring a patient flow and a patient pressure and acquiring a side-stream breath sample. The method determines a flow of the side-stream breath sample and a concentration of oxygen and a concentration carbon dioxide in the acquired side-stream breath sample. The determined flow and concentrations are temporally aligned on approximately a breath-by-breath basis.

In another aspect of the invention, a breath-by-breath analyzer is disclosed that includes a sensor constructed to engage a respiration flow. An analyzer connected to the sensor is configured to determine a pressure and at least a portion of a composition of the respiration flow. The analyzer includes an adapter that is configured to engage the sensor such that a first portion of the respiration flow passes through the sensor and a second portion of the respiration flow passes through the adapter. Such a construction provides a high-flow analyzer that is configured to monitor respiration performance on a breath-by-breath basis.

Yet another aspect of the invention includes a respiration monitoring system having an oxygen sensor constructed to detect an oxygen concentration and a carbon dioxide sensor constructed to detect a carbon dioxide concentration. The monitoring system includes first and second inputs wherein each input is constructed to fluidly connect a respective gas source to the oxygen and carbon dioxide sensors.

A respiration monitoring device according to another aspect of the invention includes at least one of valve, a pump connected to the valve, an oxygen sensor, a carbon dioxide sensor, and a control. The control is configured to control operation of the valve and pump for communicating a gas to each of the oxygen sensor and the carbon dioxide sensor to mimic a breath flow and a breath composition.

Another aspect of the invention includes a physiologic monitor controller having an input configured to receive a physiologic signal and a correction protocol configured to determine an output by adjusting a value of the input in an amplitude domain and a time domain.

Various other feature, aspects, and advantages of the present invention will be made apparent from the following detailed description and the drawings.

BRIEF DESCRIPTION OF THE DRAWINGS

The drawings illustrate one preferred embodiment presently contemplated for carrying out the invention. In the drawings.

DETAILED DESCRIPTION OF THE PREFERRED EMBODIMENT

Figure 2:
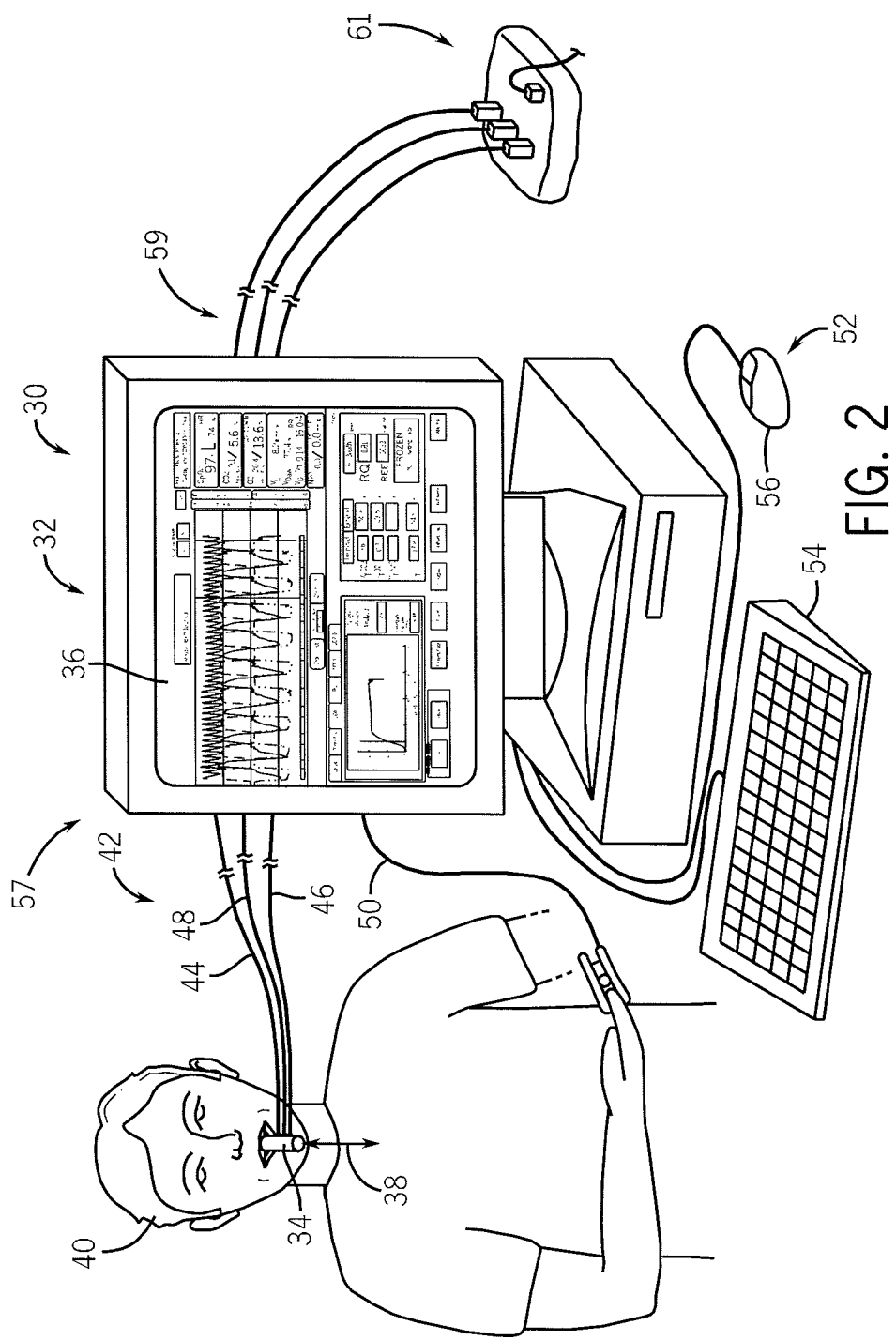
FIG. 2 is a perspective view of a side-stream respiration monitoring system according to the present invention.

FIG. 2 shows a monitoring system 30 according to the present invention. Monitoring system 30 includes a control or analyzer 32, a sensor 34, and a display 36. Sensor 34 is constructed to engage a respiration flow, indicated by arrow 38, or a participant or patient 40. A number of tubes 42 operatively connect sensor 34 to analyzer 32. A first and a second tube 44, 46 are connected to sensor 34 to detect a pressure differential of respiration flow 38 in sensor 34. A third tube 48 acquires an aspirated sample of respiration flow 38 and communicates the sample to analyzer 32. A physiological detector, preferably a heart rate monitor 50, is also connected to analyzer 32 and constructed to communicate a patient cardiac status to analyzer 32. Preferably, monitor 50 is configured to monitor both the pulsatile effects of the patient's cardiac cycle as well as the saturated oxygen content of the patient's circulation system.

Analyzer 32, having acquired the data or signals from tubes 42 and heart rate monitor 50, generates time aligned and composition corrected respiration information and outputs the information at display 36 as explained further below. Analyzer 32 includes optional user inputs 52 that allow a user to selectively configure the operation of analyzer 32 and the output of display 36 such that analyzer 32 and display 36 generate and output the desired information, respectively. It is further appreciated that display 36 can be constructed as a touch screen display such that a user or technician can manipulate the display results thereof and operation of analyzer 32 by touching selected areas of the display without utilization of auxiliary input devices such as a keyboard 54 and/or a mouse 56.

Figure 3:
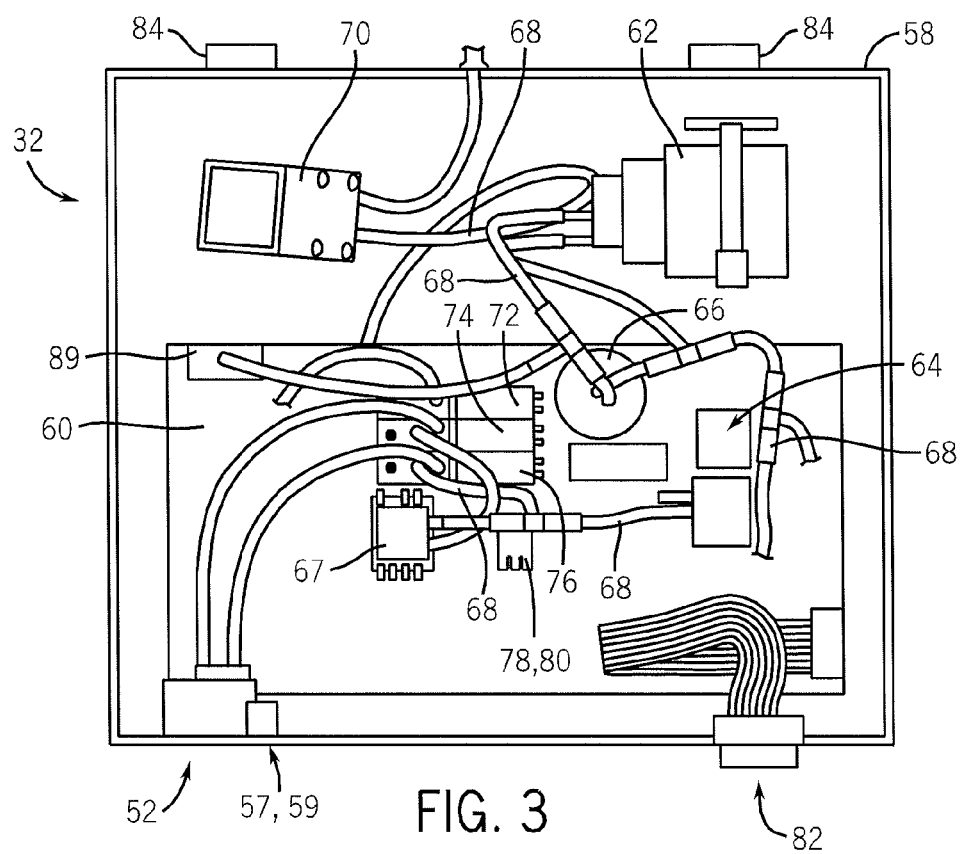
FIG. 3 is a plan view of an analyzer of the monitoring system shown in FIG. 2.

As described further with respect to FIG. 3, analyzer 32 includes a first input 57 and a second input 59 to allow multiple gas sources to concurrently be connected to analyzer 32. As shown in FIG. 2, first input 57 is connected to sensor 34 and second input 59 is connected to another sensor, a Douglas bag, gas cylinder, or container 61. It is appreciated that container 61 can be configured to contain a volume of a known gas or a volume of a gas collected from another patient. Such a configuration allows monitoring system 30 to monitor and assess multiple gas sources. Such a configuration is particularly useful in environments where monitoring of several patients is desired or where patients with reduced respiration tidal volumes, such as premature babies, have such low respiration volumes that collection of a respiration is required to assess the composition of the respiration gases.

Referring to FIG. 3, analyzer 32 includes a housing 58 having a control or controller 60 contained therein. An oxygen sensor 62, a nitrous oxide sensor 64, and a carbon dioxide sensor 66, and a flow sensor 67 are also positioned in housing 58. It is understood that oxygen sensor 62 be any of a number of technology based such as laser, acoustic, solid state, amperometric such as galvanic, or potentiometric. A number of tubes 68 interconnect sensors 62, 64, 66 and communicate respective portions of the acquired flow through the analyzer. A pump 70 and a number of valves 72, 74, 76 control the directional passage of the respiration flow through analyzer 32. Analyzer 32 includes a humidity sensor 78 and a temperature sensor 80 configured to monitor both ambient temperature and humidity as well as temperature and humidity of the respiration flow. It is further appreciated that analyzer 32 include an optional heater and/or humidifier to communicate thermal energy and/or moisture to a patient via the respiration flow.

Figure 4:
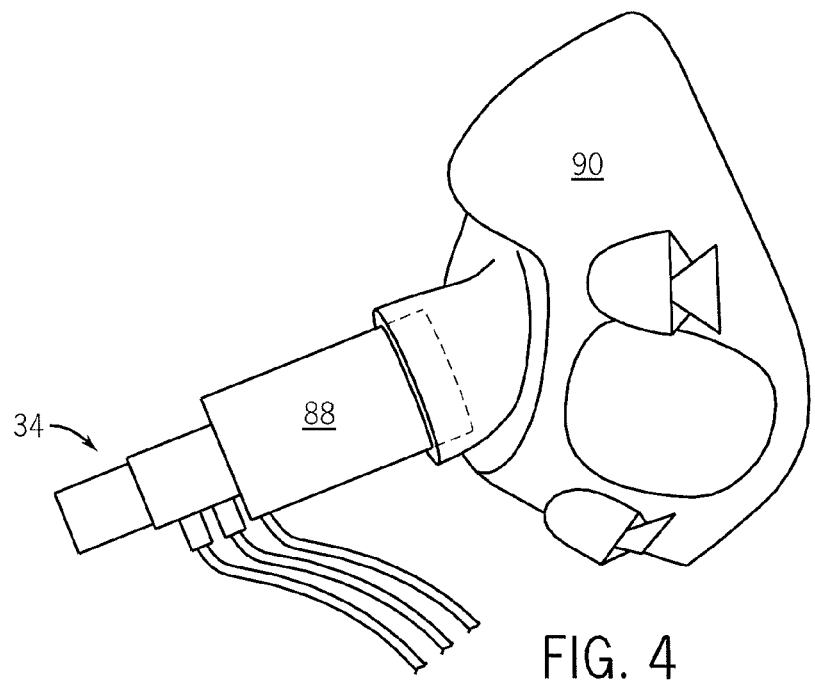
FIG. 4 is a perspective view of one embodiment of a sensor of the monitoring system shown in FIG. 1 with an optional adapter and mask attached to the sensor.

First input 57 and second input 59 extend through housing 58 and are constructed to removably engage the tubes 42 connected to sensor 34 or container 61 as shown in FIG. 2. An electrical connector 84 also extends through housing 58 and is constructed to communicate information generated by analyzer 32 to external devices such as personal computers, personal data assists (PDA's), cell phones, or the like. Alternatively, it is further understood that analyzer 32 include a wireless interface to allow wireless communication of the information acquired and calculated by analyzer 32 to external devices. Analyzer 32 includes an input connector 82 constructed to communicate information from patient monitor 50 to the analyzer. Input 84 is constructed to removably connect monitor 50 to analyzer 32 to communicate the information acquired by monitor 50 to the analyzer 32. It is understood that inputs and connectors 84 be any conventional connection protocol such as serial pin connectors, USB connectors, or the like, or have a unique configuration. Analyzer 32 further includes a leak test valve 89, the operation of which is described below with respect to the automatic calibration and performance monitoring of analyzer 32. It is appreciated that the relatively compact and lightweight nature of analyzer 32 provides a respiration monitoring system 10 that is highly portable and operable with a number of sensors. FIGS. 4-6 show a number of sensors that are applicable with the present invention.

FIG. 4 is an enlarged view of sensor 34 with an optional adapter 88 and an optional mask 90 connected thereto. Mask 90 ensures that nasal respiration is prevented or directed toward sensor 34 during a respiration monitoring procedure. Such a configuration ensures information indicative of an entire respiration flow is communicated to analyzer 32. Comparatively, adapter 88 is constructed to allow a portion of a respiration flow to bypass sensor 34. Such a configuration is particularly applicable to acquiring respiration data during periods of high respiration flow such as during adult or athlete stress testing procedures.

Figure 5A:
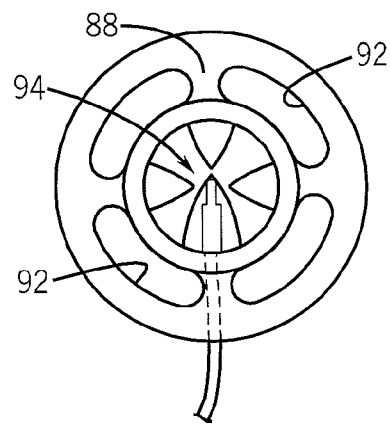
FIGS. 5a and 5b are elevational end views of the sensor shown in FIG. 4 with adapter connected to the sensor and the mask removed therefrom.
Figure 5B:
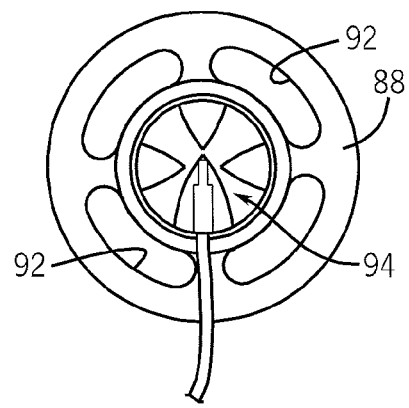
Figure 6:
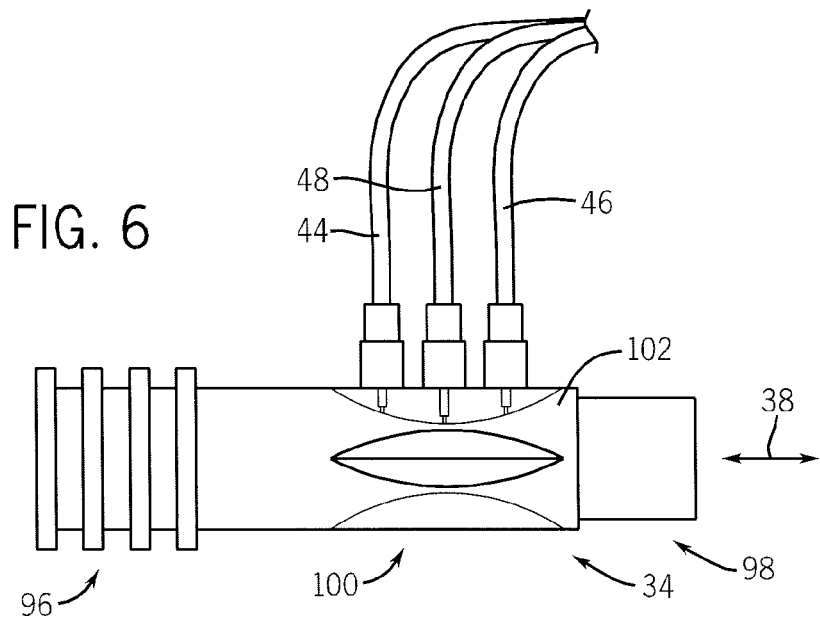
FIG. 6 is an elevational view of the sensor of the monitoring system shown in FIG. 5 with the adapter removed from the sensor.

As shown in FIGS. 5a and 5b, adapter 88 includes a number of passages 92 constructed to allow a portion of a total respiration flow to pass to atmosphere thereby bypassing a flow passage 94 of sensor 34. Preferably, adapter passages 92 are configured to allow a flow that is a multiple of the flow directed through sensor 34 to pass through adapter 88. More preferably, passages 92 are constructed to allow a multiple of ten of the respiration flow directed through sensor 34 to pass through adapter 88. Such a configuration simplifies the calculation associated with determining the total flow information when only a fraction of the total flow is directed through the sensor 34. Adapter 88 facilitates the increased respiration flow generally associated with a stress test without overly burdening the respiration system of the patient or participant associated with requiring the entirety of the respiration flow to pass through the more constricted passage of sensor 34.

FIG. 6 is a detailed view of sensor 34 with adapter 88 and mask 90 removed therefrom. Adapter 88 includes a patient end 96 and an atmosphere end 98. A sensor section 100 is generally disposed between the patient end 96 and the atmosphere end 98. Sensor section 100 includes a venturi-like section 102 constructed to generate a pressure differential between respective ends of the sensor section 100. Signals communicated to analyzer 32 via first tube 44 and second tube 46 allow analyzer 32 to detect the pressure differential across sensor section 100 and thereby provide information utilized to calculate the respiration flow 38 communicated through sensor 34. Third tube 48 acquires a sample of the respiration flow, or an aspiration, and communicates the acquired sample to the analyzer 32 which then determines the make-up or composition of the gas of the respiration flow. It is appreciated that the construction of the sensor may vary depending, in part, on a patient's respiration ability. That is, sensor 34 may be adapted to accommodate respiration monitoring of patients with low respiration tidal volumes or flows such as for analyzing respiration compositions associated with premature infants, neonatal patients or the like. For such applications sensor 34 may be configured to operate at a flow resistance over a differential pressure range of approximately 0-16 cm water which covers a smaller flow range generally in the range of 0 to ten liters per minute. Further details of the construction and operation of sensor 34 are disclosed in Applicant's U.S. Pat. No. 5,925,831 and D413,825 and U.S. Publication No. 2004/0254491, all of which are incorporated herein by reference.

Figure 7A:
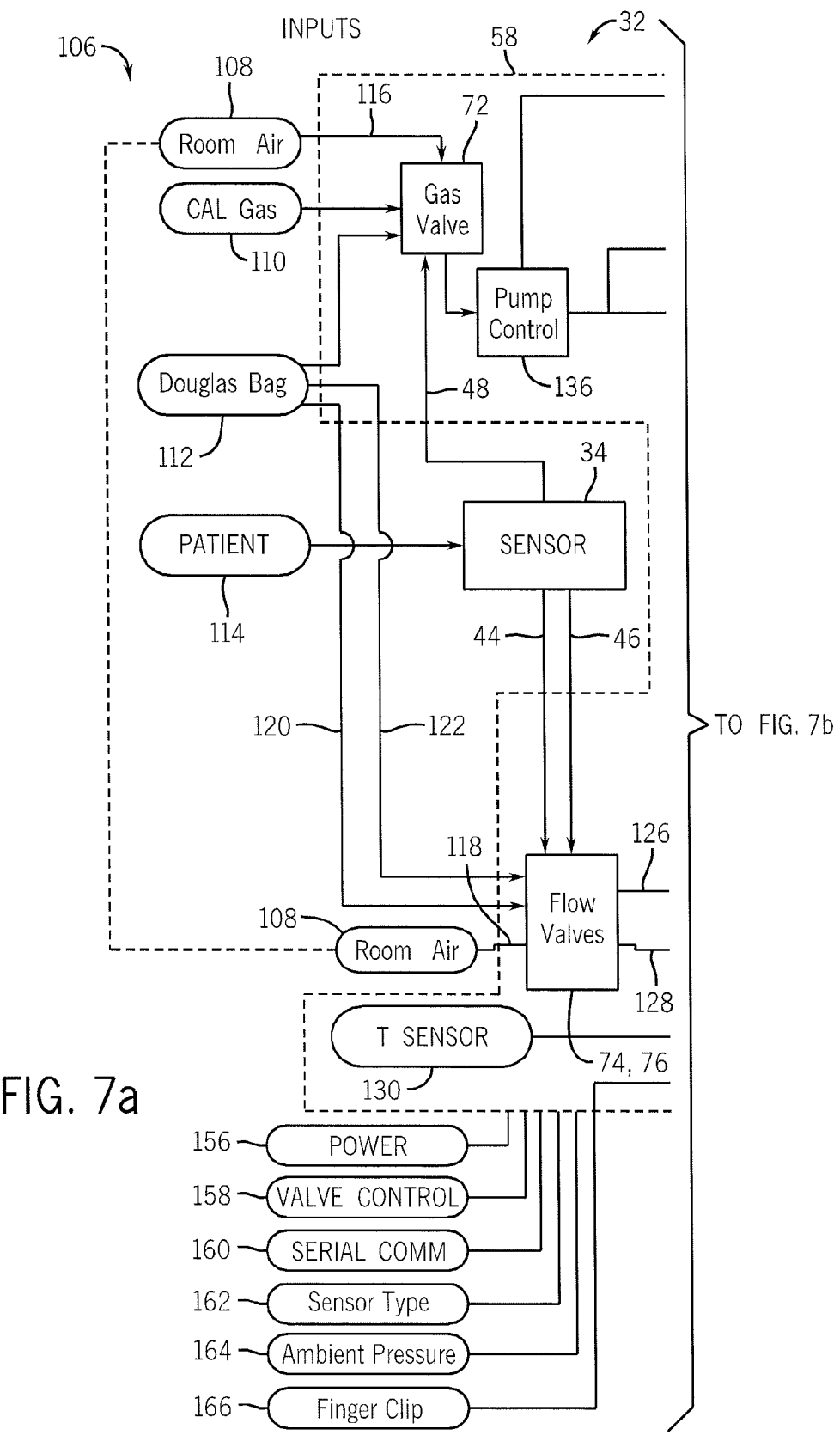
FIGS. 7a and 7b are a schematic representation of the monitoring system shown in FIG. 2.
Figure 7B:
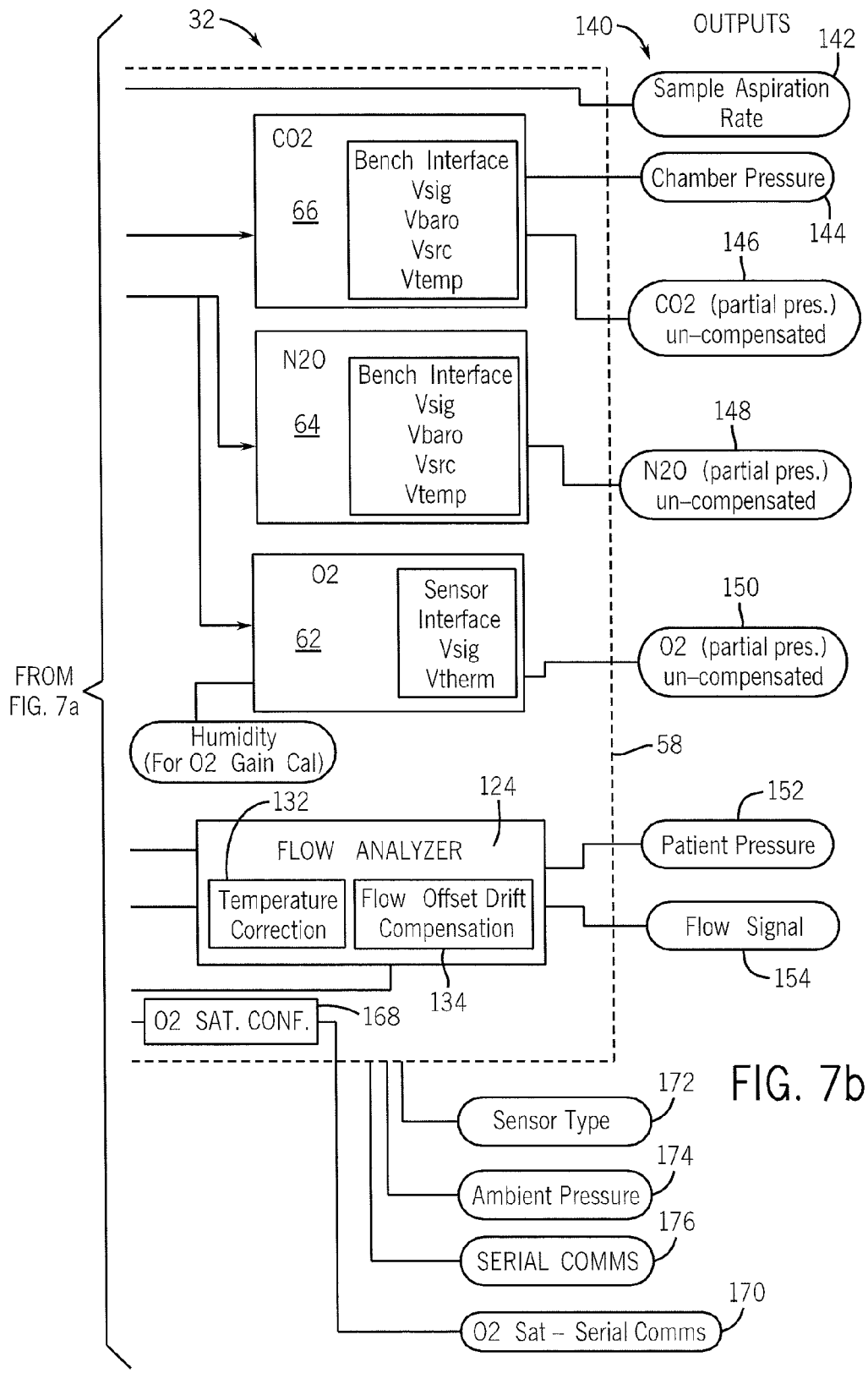

FIG. 7 shows a schematic representation of sample flow through analyzer 32. Analyzer 32 is constructed to receive any of a number of inputs 106 associated with a gas to be analyzed. Inputs 106 can include a room air or ambient input 108, a calibration gas input 110, a Douglas bag input 112, and a patient input 114. A first tube 116 communicates ambient input 108 to gas valve 72 and a second tube 118 communicates ambient input 108 to flow valves 74, 76 of analyzer 32. Similarly, tubes 44 and 46 connected to sensor 34 communicate patient flow-to-flow valve 74 and 76. When a Douglas bag input 112 is utilized with analyzer 32, a first tube 120 and a second tube 122 communicate a Douglas bag gas material to valves 74, 76. Understandably, it is appreciated that a Douglas bag is a container configured to store a respiration sample or a known expiration sample.

Regardless of the source of the input gas, flow valves 74, 76 communicate the received flow to a flow analyzer 124 via tubes 126, 128. Flow analyzer 124 is connected to a temperature sensor 130 and includes a temperature correction protocol 132 configured to detect and associate a detected flow with a respective temperature of the analyzer 32 or atmosphere. Temperature correction protocol 132 corrects the calculated flow value for variable temperatures associated with the test environment. Flow analyzer 124 includes a flow offset drift compensator 134 figured to account for drift variations associated with extended operation of analyzer 32. Accordingly, flow analyzer 124 is configured to adjust the measured flow parameter for variations associated with ambient conditions as well as operational variation of the flow analyzer 124.

Gas samples that are communicated to gas valve 72 are communicated to a pump control 136 and therefrom to each of oxygen sensor 62, nitrous oxide sensor 64, and carbon dioxide sensor 66. Oxygen sensor 62, nitrous oxide sensor 64, and carbon dioxide sensor 66 are configured to indicate the respective levels of the constituent gases contained in the input flow regardless of the source of the input gas. Accordingly, analyzer 32 is operable with a number of gas sources that can be concurrently connected to the analyzer 32. As will be described further, controller 60 is configured to assess which type of gas source is connected to the analyzer and initiate a monitoring sequence or a calibration sequence.

Still referring to FIG. 7, analyzer 32 generates a number of outputs 140, including a sample aspiration rate 142 that is derived from pump control 136. A chamber pressure value 144 and an uncompensated carbon dioxide value 146 are derived from carbon dioxide sensor 66. An uncompensated nitrous oxide value 148 is derived from nitrous oxide sensor 64 and an uncompensated oxygen value 150 is generated from oxygen sensor 62. Flow analyzer 124 generates patient pressure data 152 and respiration flow data 154. Analyzer 32 also includes a plurality of user inputs that include a power input 156, a valve control input 158, a serial communication input 160, a sensor-type selection 162, an ambient pressure input 164 and a patient finger clip 166 configured to monitor patient cardiac condition.

Analyzer 32 includes an oxygen saturation controller 168 that determines a patient oxygen saturation level communicated to the oxygen saturation controller 168 from an oxygen saturation serial communication link 170 constructed to engage the patient monitor 50. Analyzer 32 is also configured to generate an output associated with a sensor type 172 and an ambient pressure determination 174. As discussed above, analyzer 32 includes a number of serial communication links 176 that facilitate connectivity between analyzer 32 and other auxiliary devices such as personal computers, PDA's and the like. Such a configuration allows analyzer 32 to operate with a number of different flow input sources, be configured to operate with a number of gas and flow sensors, and provide a number of variable format outputs. Analyzer 32 is constructed to be dynamically responsive to the gases communicated to the analyzer, the connectivity modalities associated with the separable components of the monitoring system, and providing data that is in a user desired format.

Figure 8:
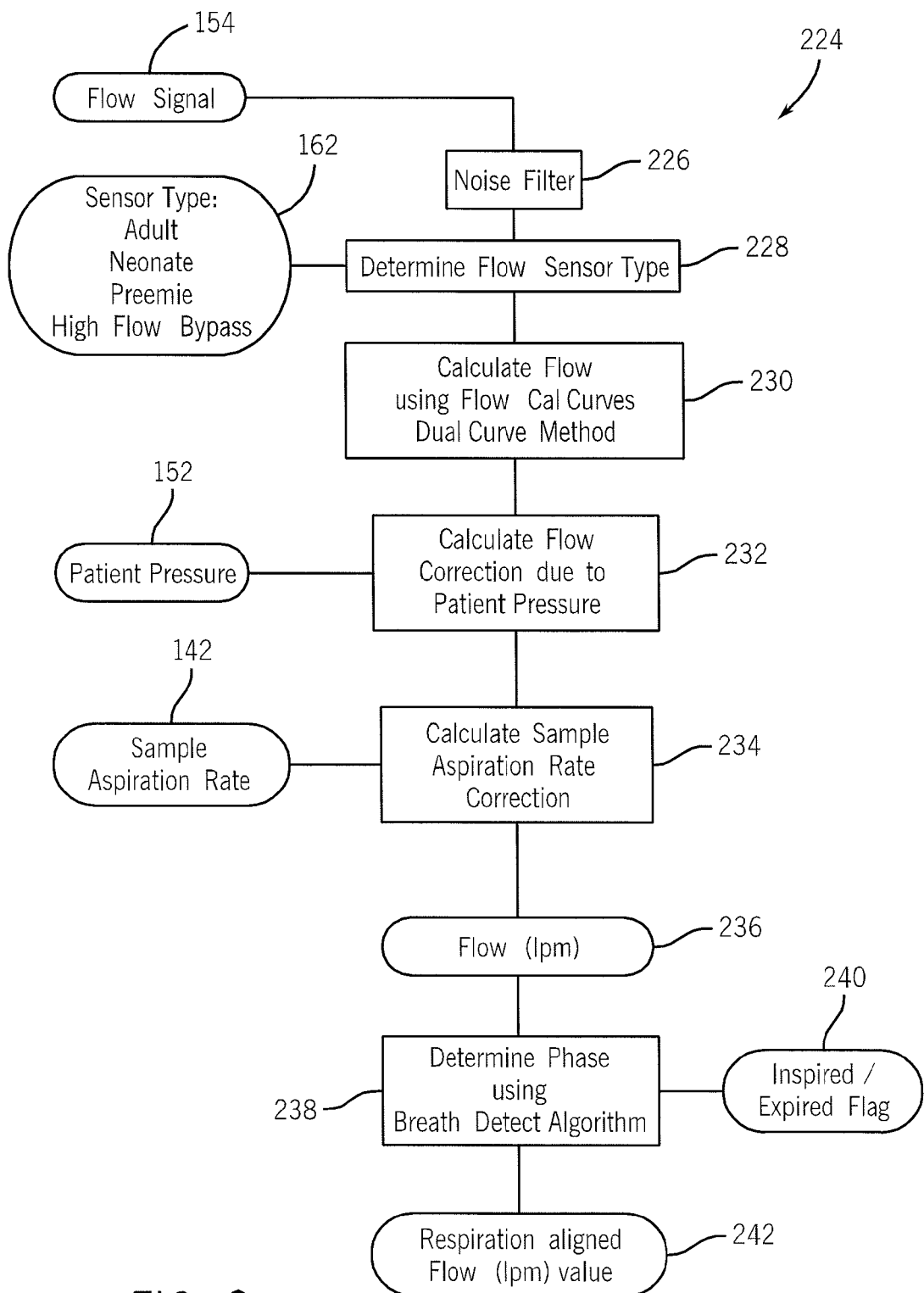
FIG. 8 is a schematic representation of a flow determination correction procedure performed by the monitoring system shown in FIG. 2

Analyzer 32 includes a flow determination and correction protocol 224 as shown in FIG. 8. Correction protocol 224 acquires respiration flow data 154 from flow analyzer 124 as shown in FIG. 7. A noise filter 226 addresses electrical signal noise associated with operation of flow analyzer 124. Correction protocol 224 is also configured to determine a sensor type 228 associated with acquisition of the flow. That is, the determination of the flow sensor type 228 determines whether the sensor is constructed to receive the respiration flow of an adult, a neonatal or infant, a premature baby, or a high-flow, i.e., bypass sensor configuration as previously described with respect to FIGS. 2-7.

Correction protocol 224 calculates the respiration flow 230 using a flow calculation curve as described below. A patient pressure flow correction 232 is calculated from the patient pressure data 152 as determined by flow analyzer 124. A sample aspiration rate correction 234, is implemented and utilizes the sample aspiration rate 142 generated from pump control 136 as shown in FIG. 7. Having calculated and corrected the flow based on patient pressure and aspiration rate correction, correction protocol 224 determines a respiration flow value 236 associated with each breath cycle of a monitored respiration cycle. The flow value 236 is then temporally aligned with a respiration phase 238 using an inspired/expired flag 240 as acquired from the respiration cycle. Having determined the phase of the associated flow value, correction protocol 224 generates a respiration aligned flow value 242 indicative of the flow value at any given time during a respiration cycle.

Figure 9:
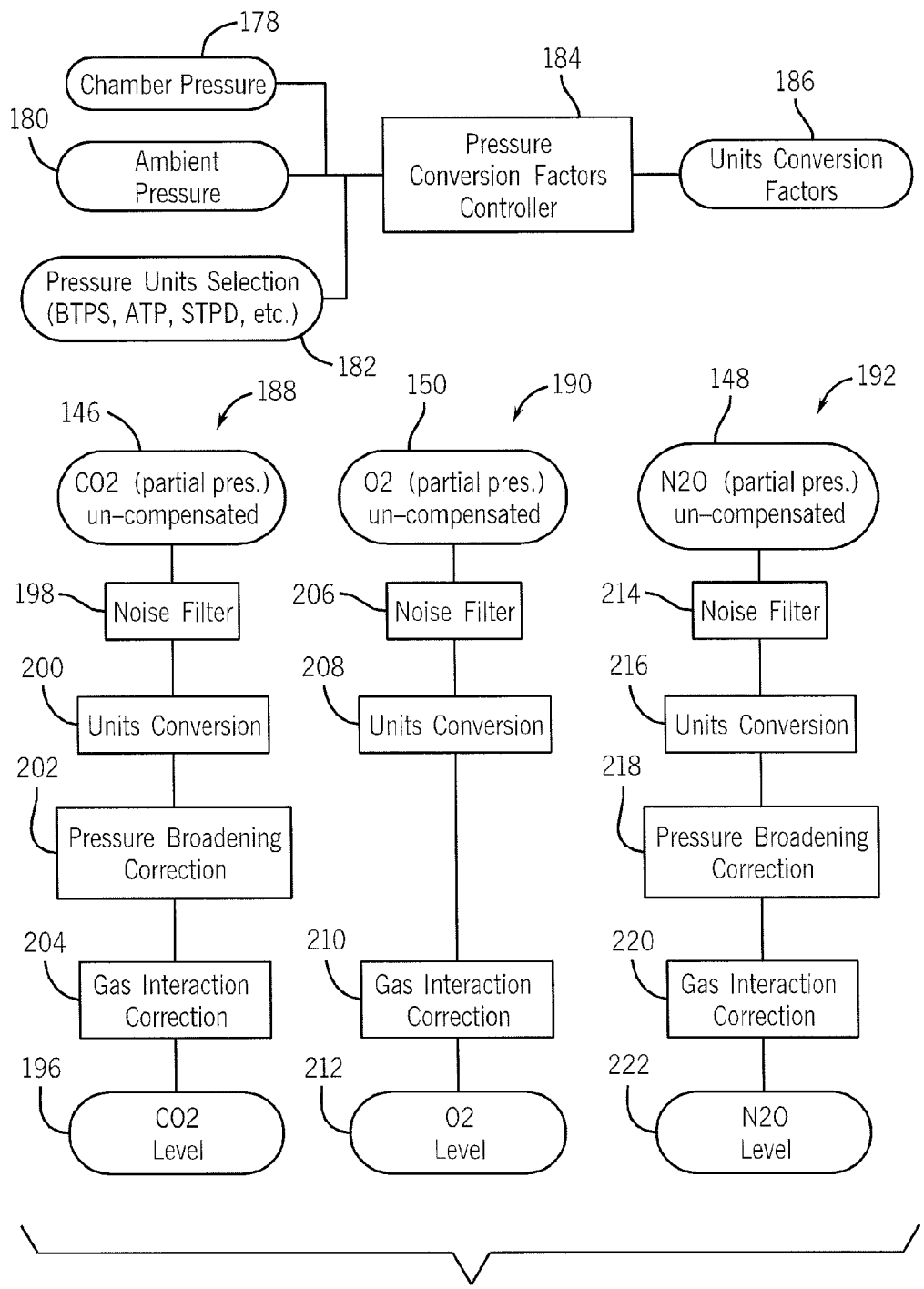
FIG. 9 is a schematic representation of a series of first composition correction operations performed by the monitoring system shown in FIG. 2.

FIG. 9 shows a number of first data correction procedures performed by analyzer 32. As discussed above with respect to FIG. 7, analyzer 32 is constructed to detect a chamber pressure 178, an ambient pressure 180, and is responsive to a pressure units selection 182. These parameters are input to a pressure conversion factor controller 184 that is configured to output a corrected detected pressure in desired units 186. Analyzer 32 also includes a carbon dioxide correction protocol 188, an oxygen correction protocol 190, and a nitrous oxide correction protocol 192. Carbon dioxide correction protocol 188 adjusts a respiration carbon dioxide value 194 by passing the uncompensated carbon dioxide value 146 through a noise filter 198, a unit converter 200, a pressure-broadening correction 202 and a gas interaction correction 204. Noise filter 198 is constructed to resolve electrical noise associated with operation of the carbon dioxide sensor 66. Unit converter 200 is constructed to convert the carbon dioxide value to user-desired units. Pressure broadening correction 202 is constructed to further adjust the uncompensated carbon dioxide value 146 with respect to operation of the carbon dioxide sensor 66 at the system, environment, or ambient operating pressure.

Gas interaction correction 204 corrects the uncompensated carbon dioxide value 146 for misrecognition of other gas molecules as carbon dioxide molecules. That is, due the nature of the operation of the carbon dioxide sensor 66, nitrous oxide molecules may occasionally be recognized by carbon dioxide sensor 66 as carbon dioxide molecules. Gas interaction correction 204 adjusts the uncompensated carbon dioxide value 146 for such occurrences to provide a carbon dioxide level 196 that is adjusted for these molecule misrecognition events.

Oxygen correction protocol 190 also includes a noise filter 206 configured to correct the uncompensated oxygen value 150 generated or provided by oxygen sensor 62. Noise filter 206 addresses the electrical noise associated with operation of oxygen sensor 62. A unit's conversion 208 is configured to provide an oxygen value associated with a desired user oxygen value units. Similar to gas interaction correction 204, oxygen correction protocol 190 includes a gas interaction correction 210 configured to correct the uncompensated oxygen value 150 for occurrences of oxygen sensor 62 interpreting non-oxygen molecules as oxygen. Oxygen correction protocol 190 generates an oxygen level value 212 that has been corrected for electrical noise associated with operation of the sensor 62. Similar to carbon dioxide correction protocol 188, nitrous oxide correction protocol 192 corrects an uncompensated nitrous oxide value 148 through utilization of a noise filter 214, a unit's conversion 216, pressure broadening correction 218 and a gas interaction correction 220 to provide a nitrous oxide level value 222 that more accurately reflects an actual amount of nitrous oxide contained in a respiration or gas sample and a value that has been corrected for the background noise associated with operation of the nitrous oxide sensor 64 and is in a user desired units. The nitrous oxide value has also been corrected for atmospheric and operational pressure differentials, and non-nitrous oxide gas interaction correction.

Figure 10:
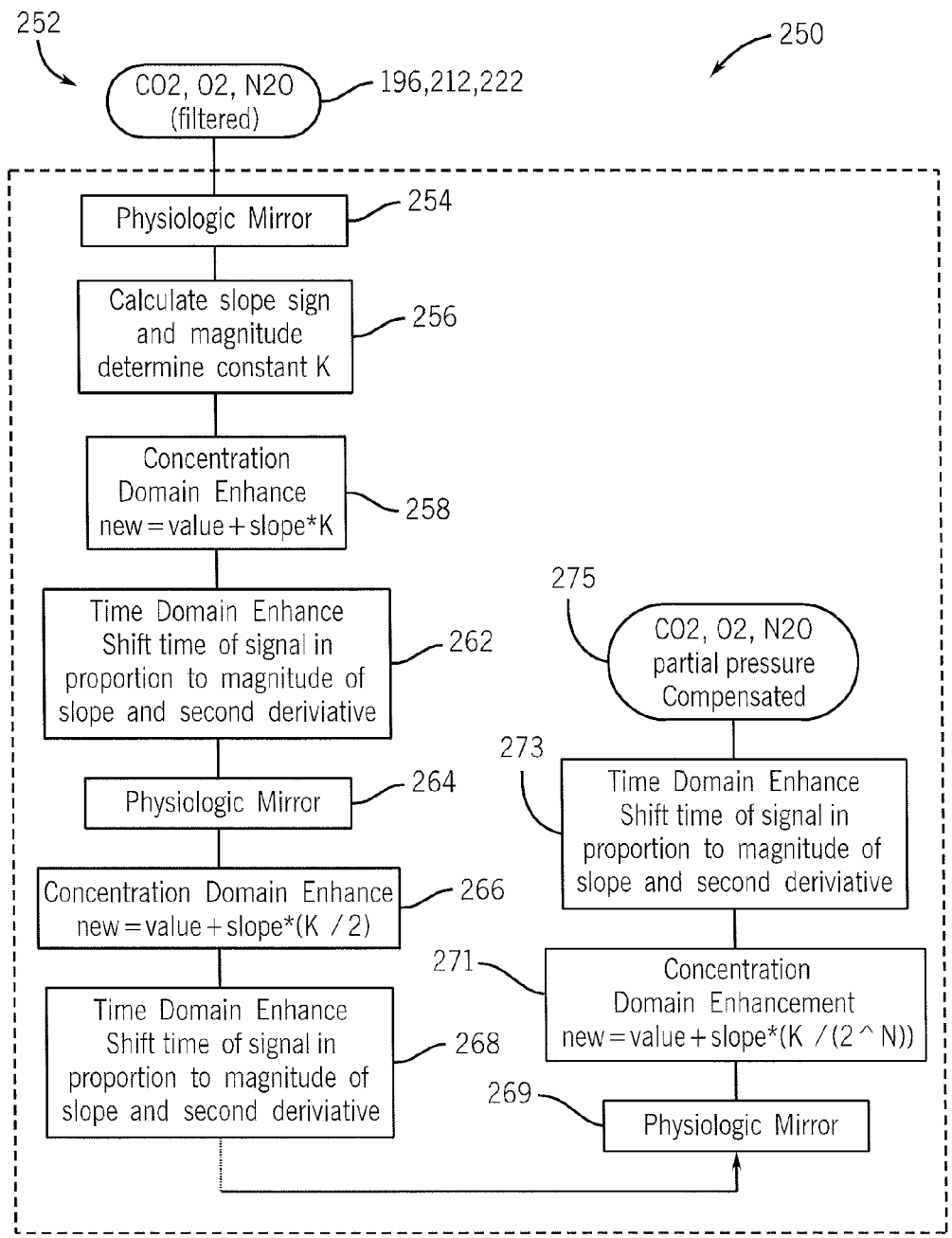
FIG. 10 is a schematic representation of a second composition correction procedure performed by the monitoring system shown in FIG. 2.

FIG. 10 shows a response time and enhancement protocol 250 performed by analyzer 32 for each of the carbon dioxide level 196, oxygen level value 212 and nitrous oxide level value 222 calculated as shown in FIG. 9. As shown in FIG. 10, response time protocol 250 receives an input 252 associated with the level values 196, 212, 222 which are associated with the respective gas levels in any given sample. Inputs 252 are verified and adjusted via a physiological mirror 254 as described further below. Protocol 250 calculates a slope sign and magnitude-determined constant K 256 for each input 252 associated with the respective gas. A concentration domain enhancement 258 is generated for each input 252. The slope of the acquired data signal is determined, for example based on the signal change over the last ten samples, and, if the slope is flat or approximates zero, the constant K is chosen to be zero. By first qualifying the state of the rate of change of the signal, analyzer 32 avoids amplifying noise which would occur if a uniform K value were applied regardless of the instantaneous sample change. When the signal slope changes significantly, due to a fast rising or falling edge, constant K is computed to be generally proportional to the slope change of the concentration and proportional to accumulated flow volume up to a maximum allowed value. The interaction of the flow volume in addition to the change in concentration information is used to qualify constant K.

Figure 11:
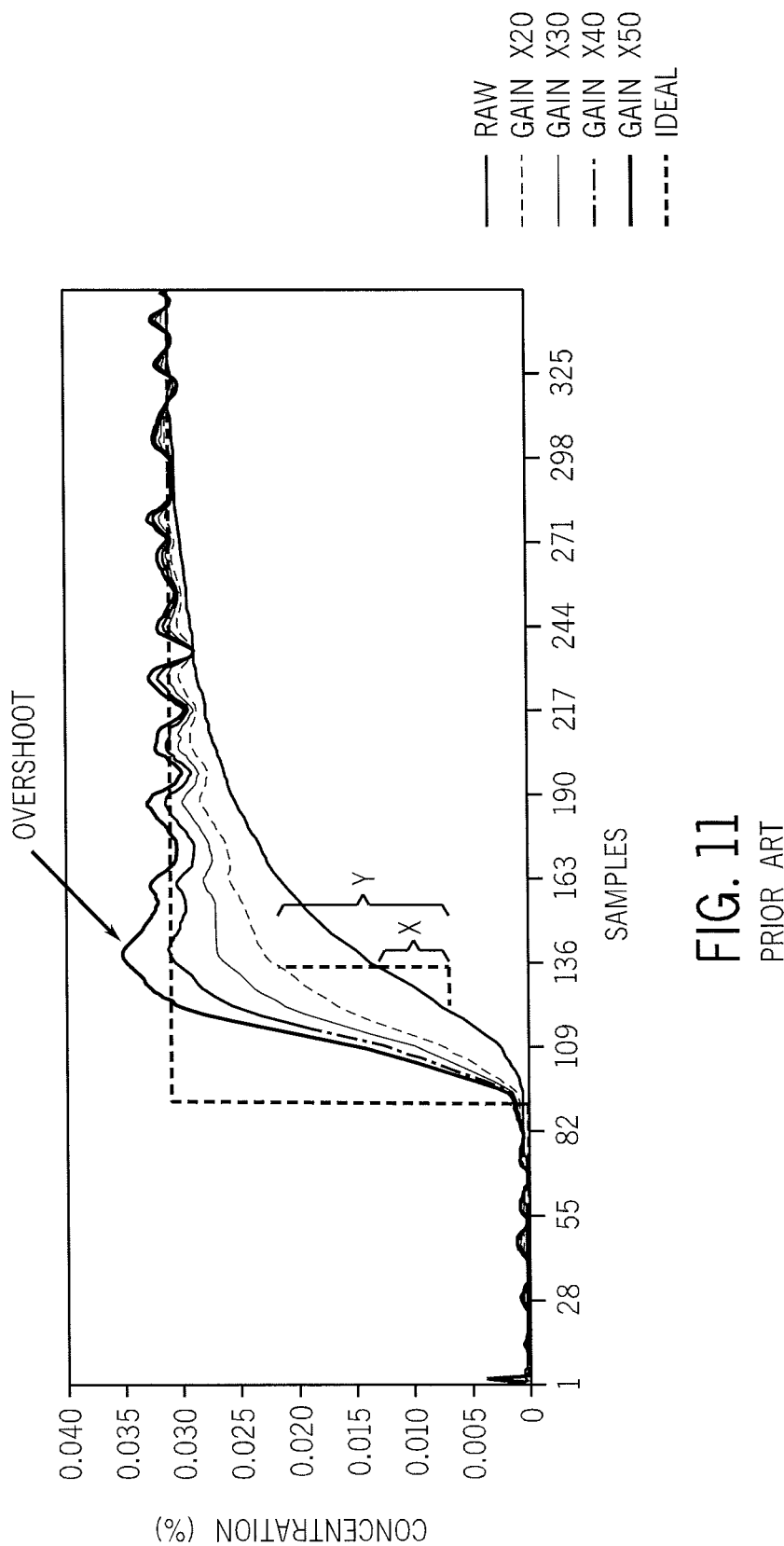
FIG. 11 is a graphic representation of a concentration domain response time enhancement achieved with prior art respiration monitoring systems.

FIG. 11 shows a problem associated with prior art concentration domain response time enhancement procedures that are overcome by the present invention. Usually, a speed-up circuit, or its equivalent in software, is employed in the concentration domain. That is, if the rise at the analyzer is x, then the actual rise at the aspiration location must have been at least y wherein y is a value greater than x. FIG. 11 shows that if gain concentration enhancement of gain times 20 is used, a change in concentration X would result in a reported concentration Y over the same time interval. This approach has severe limitations in that it attempts to compensate a function of concentration versus time by only adjusting the information in one axis. To reproduce a very fast rise, say that which is generated by a square wave input at the aspiration site, overshoot occurs long before a squared output can be obtained. This overshoot is often followed by ringing of the function about the final value before settling occurs thereby detracting from the responsiveness of the system. As shown, simply reducing the gain factor does not reproduce what occurred at the aspiration site but merely reduces the amount of the overshoot and ringing or signal bounce.

Figure 12:
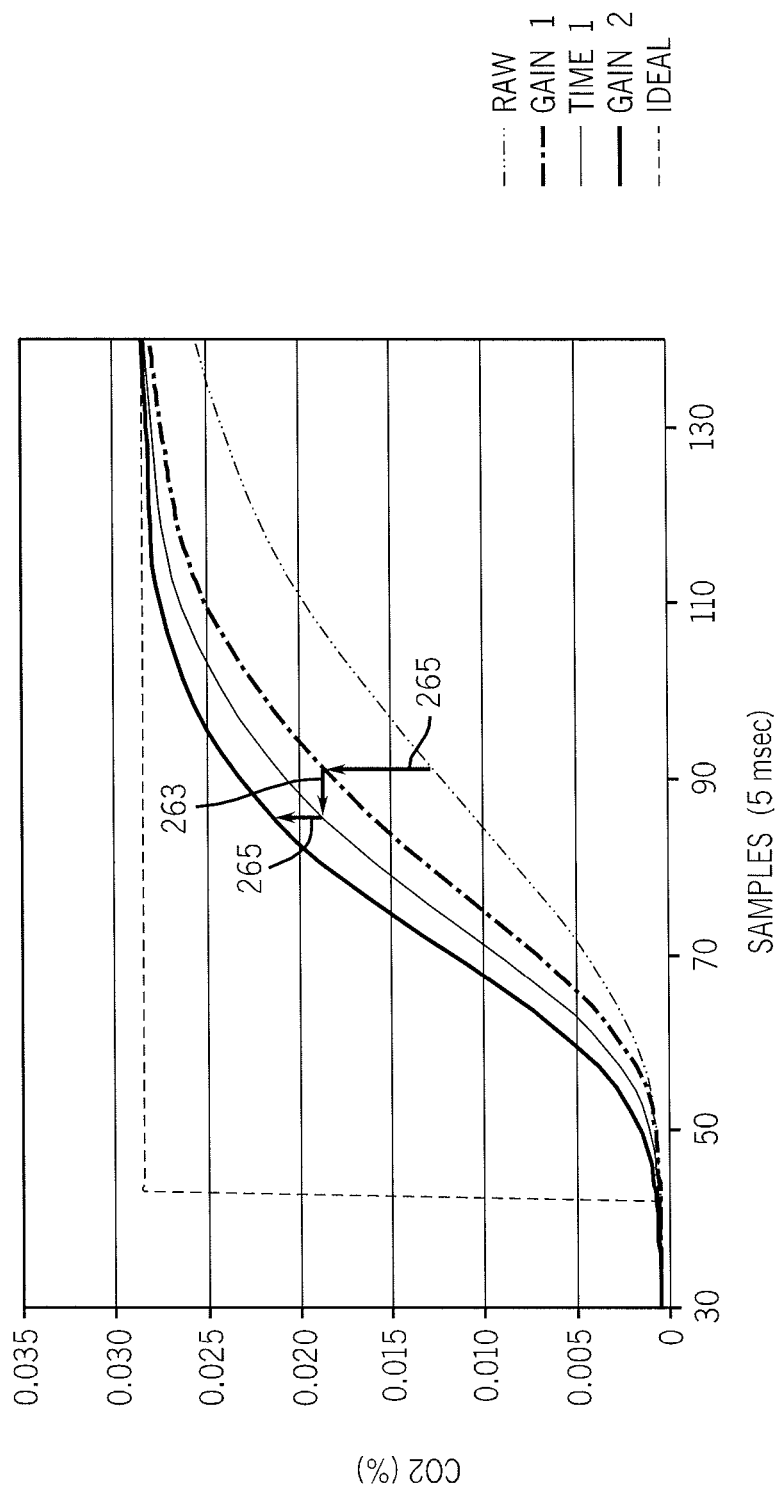
FIG. 12 is a graphic representation of a sample time response time enhancement achieved by the respiration monitoring system shown in FIG. 2.

Referring to FIGS. 10 and 12, unlike the solely concentration domain enhancement results shown in FIG. 11, response time enhancement protocol 250 adjusts for variable gains associated with any of the respective input 252. Having acquired the concentration domain enhancement 258, enhancement protocol 250 performs a time shift of the signal in proportion to the magnitude of slope and a second derivative 262 associated with inputs 252. After the signal is enhanced in the concentration domain, the signal is enhanced in the time domain. Analyzer 32 calculates the first and second derivative of the signal and computes incremental time points from the first and second derivative magnitudes. This manipulation pushes the start of the signal ahead in time, while the upper part of the signal, where the signal begins to plateau, gets retarded in time such that there is no residual time shifting when the slope returns to zero.

As shown in FIG. 12, for samples acquired every five milliseconds, the carbon dioxide trend is adjusted for multiple gains, indicated by arrows 263, 265 across an acquisition cycle. Each correction protocol 188, 190, 192 performed by controller 60 of analyzer 32 is configured to determine a parameter output value by adjusting a value of an input, i.e. the detected value, in both an amplitude domain 265 and a time domain 263. It is appreciated that the amplitude domain 265 can be any of a concentration, a temperature, a pressure, or a flow value associated with the acquired data. It is further understood that when the amplitude domain 265 is a concentration, the associated value is the detected concentration of a gas of interest such as oxygen, carbon dioxide, nitrous oxide, or water vapor. It is further appreciated that each correction protocol 188, 190, 192 be configured to the type of sensor being utilized. That is, the correction protocol will not be the same for a laser-type oxygen sensor as compared to the galvanic-type oxygen sensor.

Figure 13A:
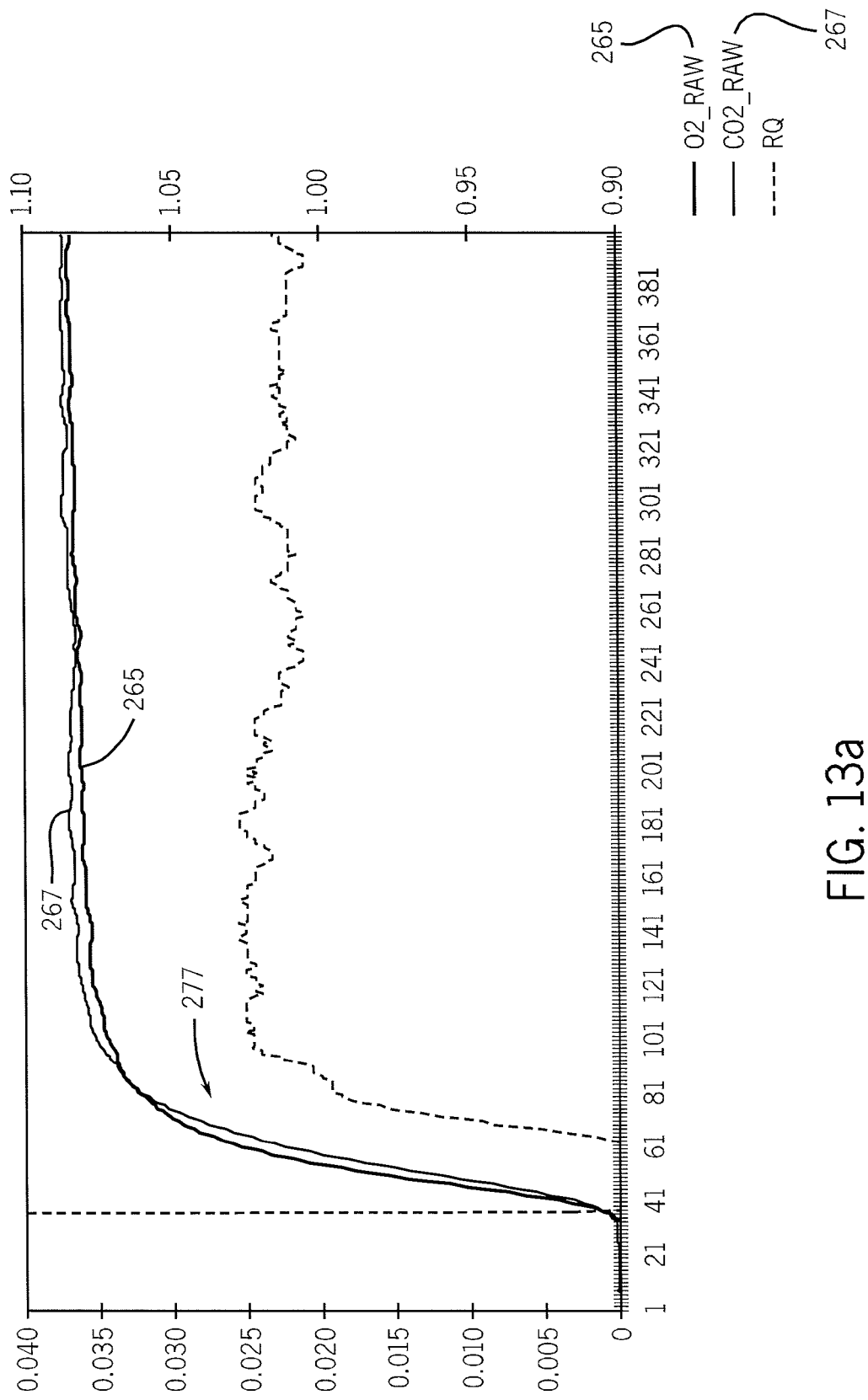
FIGS. 13a and 13b are a graphic representation of a data correction process performed by the analyzer shown in FIG. 3.
Figure 13B:
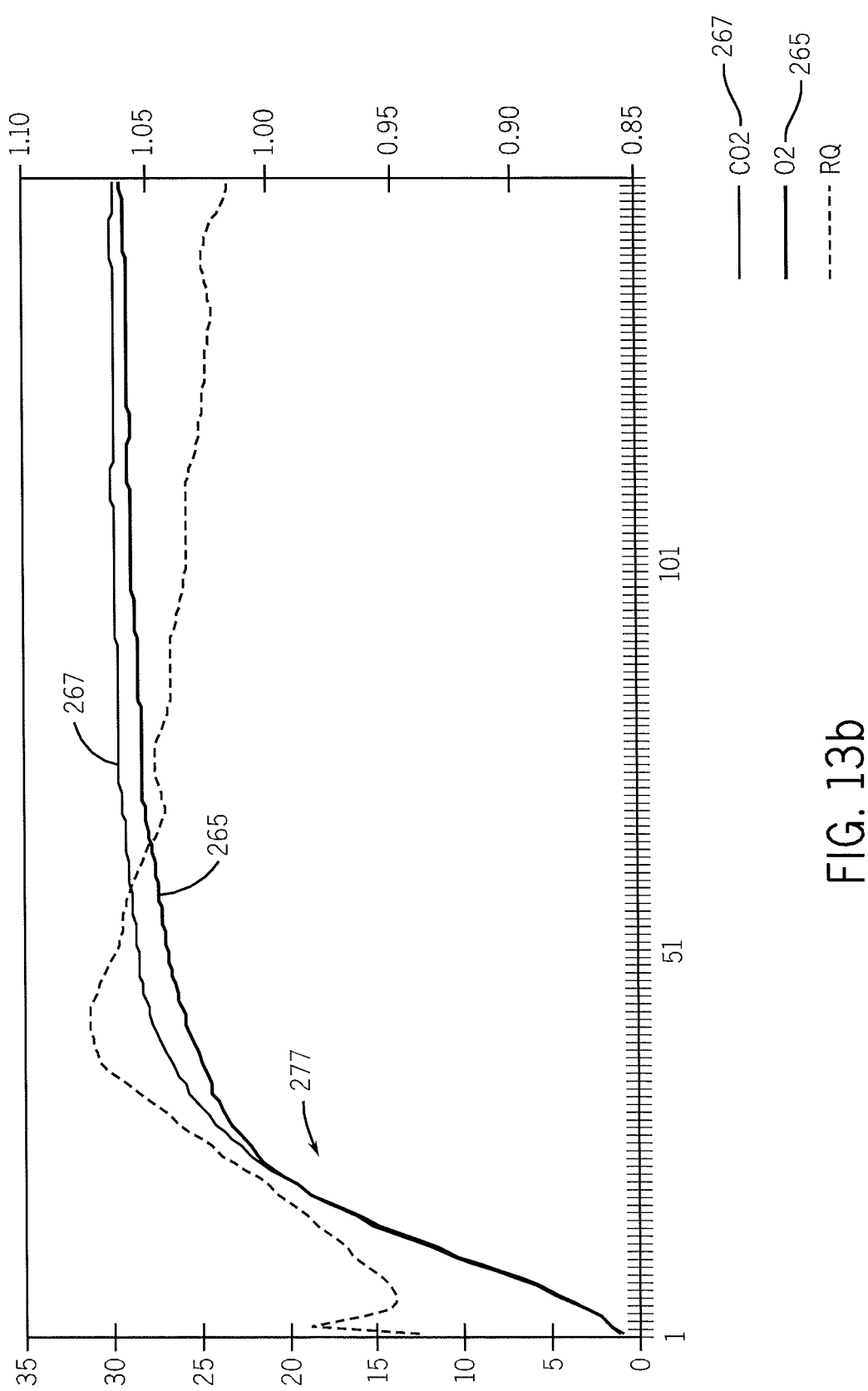

FIGS. 13a and 13b show uncorrected data and an exemplary first corrected output associated with use of a galvanic-type oxygen sensor, respectively. As shown in FIG. 13a, due in part to sensor selection and construction, the responsiveness as well as the gain accuracy of the respective sensors must be corrected. FIG. 13a shows an uncorrected fractional percentage of an oxygen deficit value 265 and an uncorrected fractional percentage carbon dioxide value 267. During a first portion of the data acquisition cycle 277, oxygen sensor 62 is more responsive than the carbon dioxide sensor 64 resulting in oxygen value 265 remaining to the left of the carbon dioxide value 267. After a given period, gain deviation of the oxygen sensor 62 results in the oxygen deficit data value falling below the carbon dioxide value 267. This operational variation of the sensors results in a deviation in the respiratory quotient value. These offsets, generally associated with the operation gain of the sensors, can be accounted for in a relatively simple manner over extended data acquisition cycles, however, these operational variations should be addressed to improve the accuracy of the real-time breath-by-breath monitoring.

FIG. 13b shows an output associated with a first correction of a response time characteristic. As shown in FIG. 13b, adjusting oxygen deficit values 265 during portion 277 of the data acquisition cycle achieves the alignment of the fractional percentage of carbon dioxide value 267 and the deficit fractional percentage of the oxygen value 265 such that the two values generally correlate as determined by the RQ value. During operation, analyzer 32 determines a maximum slope of a leading edge of the acquired oxygen and carbon dioxide values. A difference in the abscissa value associated with a line corresponding to the maximum slope provides an oxygen to carbon dioxide offset value. This offset value is applied to generally align the carbon dioxide and deficit oxygen values over portion 277 of the data acquisition cycle. To align the portion of the acquisition cycle beyond portion 277, analyzer 32 generates a gain prediction associated with operation of each of oxygen sensor 62 and carbon dioxide sensor 64. The oxygen sensor gain value is then determined to account for the deviation between the operation of the carbon dioxide sensor and the oxygen sensor over an extended duration such that the deficit oxygen value correlates to the carbon dioxide value over nearly the entirety of the data collection cycle. That is, the first correction corrects for a response time difference between the pair of sensors and the second correction is different than the first correction and corrects for another response time characteristic, i.e. gain differentiation between the respective sensors.

Referring back to FIG. 10, protocol 250 performs a second physiological mirror 264 on the time adjusted concentration values. Procedure 250 performs a second concentration domain enhancement 266 and a second time domain enhancement 268 time shift in proportion to the magnitude and slope of the second derivative. After the second time domain enhancement 268, protocol 250 again updates the data with a physical mirror check 269 and adjusts the data with a concentration domain enhancement 271 wherein constant K is divided by an exponential increase of half of the constant K utilized at enhancement 258. Process 250 further adjusts the time domain enhancement shift 273 in proportion to the magnitude of the slope and the second derivative prior to completion 275 of the time enhancement protocol 250. Upon completion 275 of protocol 250, analyzer 32 generates a partial pressure compensated gas concentration for each of the inputs 252 associated with the gasses communicated to analyzer 32.

Having corrected the respective gas values for partial pressure and temporal delays in the operation of the sensors 62, 64, 66, analyzer 32 verifies the calculated data through application of a physiological mirror comparison. That is, dynamic alignment is needed to account for differences between internal, pneumatic connections, resistances and dead-space volumes associated with the sample gas acquisition. This compensation becomes more important if there are more than one gas species to be analyzed. It is commonly understood that for every oxygen molecule consumed in a living organism, there is some concomitant generation of carbon dioxide. The exact relationship of these quantities is based upon the stoichiometric relationship of the associated gas. Because the chemical makeup of proteins, carbohydrates, fats, etc. is different, the exact relationship of oxygen to carbon dioxide is different. However, there are some aerobic physiologic ranges which cannot be exceeded and therefore generate a physiologic mirror between the associated gases. It is generally accepted that the physiologic mirror of the association carbon dioxide to oxygen during human respiration is approximately between 0.66 and 1.3 for humans at rest.

Analyzer 32 utilizes this physiological mirror to align the signals of different gas sensors as well as for filtering the signals associated with the respective sensors by identifying anomalies in the physiological mirror. Analyzer 32 is preferably configured to acquire and analyze a gas sample every five milliseconds. Analyzer 32 collects and corrects flow and gas concentration data as well as other information such as patient pressure and temperature and computes the carbon dioxide produced and the oxygen consumed for each sample acquired. The division of the carbon dioxide value by the oxygen value provides a respiratory quotient (RQ) for each sample acquired. By calculating the respiratory quotient every sample cycle, any misalignment of the respective outputs of the gas sensors becomes readily apparent and can be adjusted for. This process provides an indication as to the operating condition of the analyzer 32.

Figure 14:
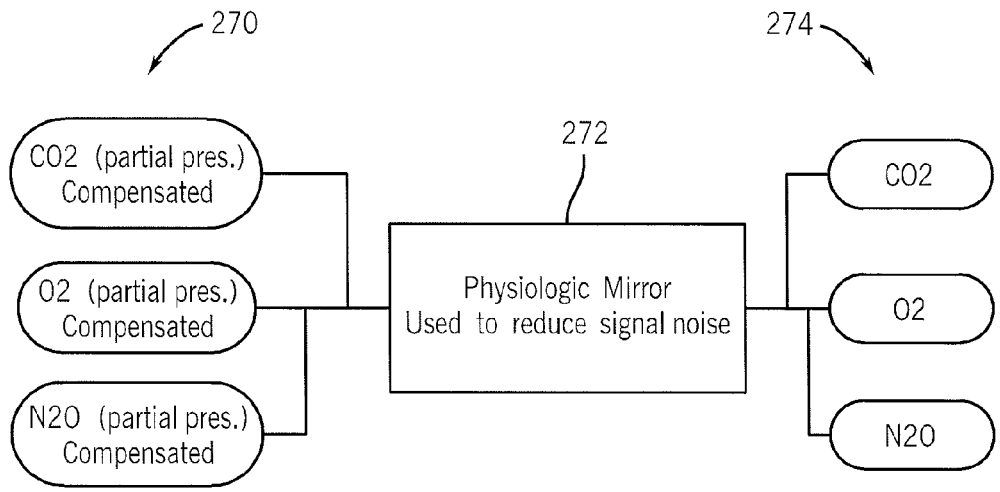
FIG. 14 is a schematic representation of a gas concentration physiological mirror correction procedure performed by the monitoring system shown in FIG. 2.
Figure 15:
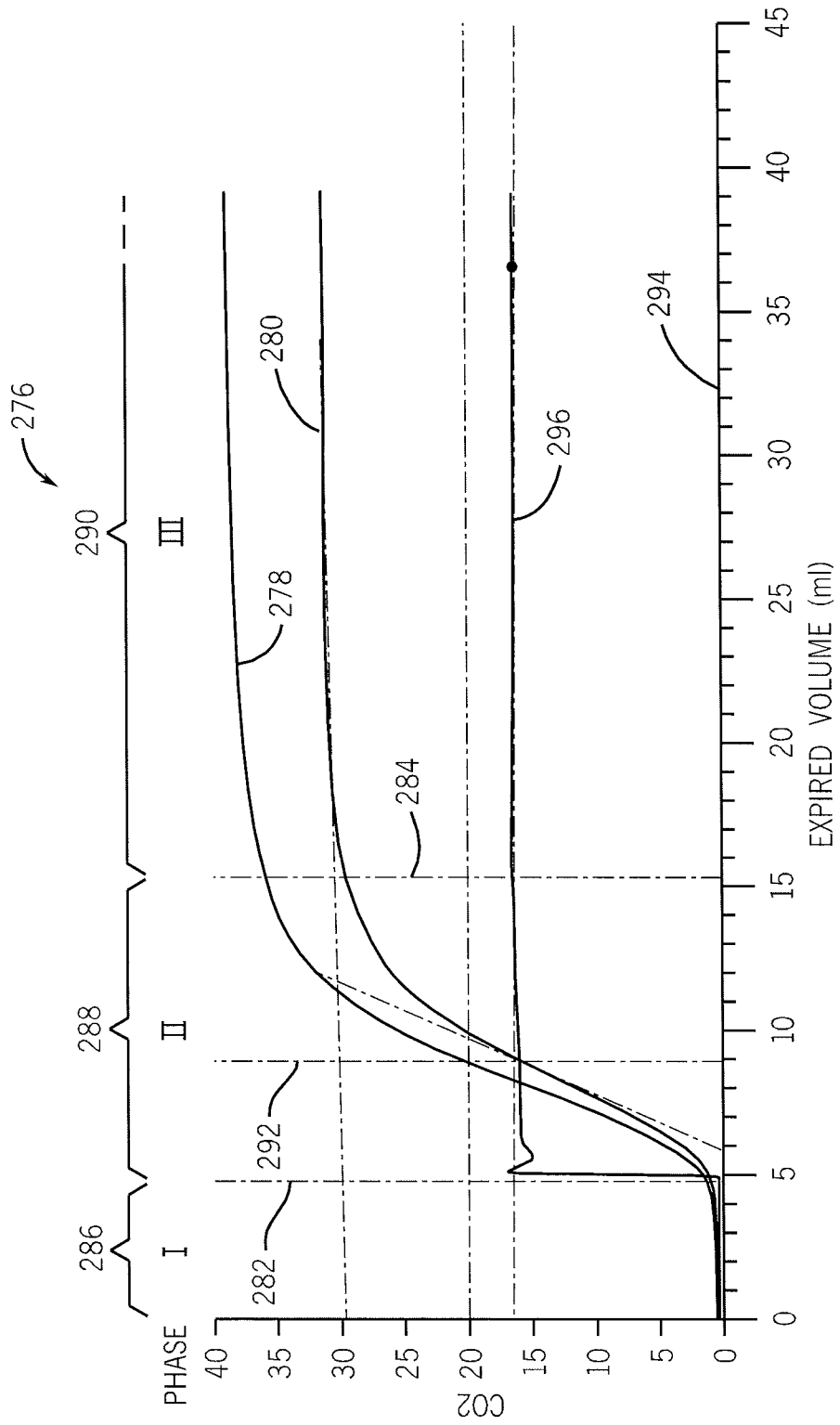
FIG. 15 is a graphic representation of one embodiment of a dead-space correction procedure achieved by the respiration monitoring system shown in FIG. 2.

As shown in FIG. 14, partial pressure compensated values 270 of the respective sample constituents, a process using a physiological mirror 272 as described above to provide a further corrected output 274 associated with each of the respective constituent sample gases. Referring to FIG. 15, analyzer 32 also includes a dead-space compensation protocol. A plot 276 showing an Aitkin dead-space shows one exemplary output associated with a dead-space calculation. Other procedures, such as the Bohr method and/or consideration of a patient's arterial carbon dioxide concentration obtained from blood gas sampling method, are equally applicable to the present invention. Instead of viewing a sample against time, plot 276 shows a gas concentration as a function of expired volume.

The particular breath shown in FIG. 15 shows an oxygen consumption trend 278 which represents inspired volume minus concentration as volume increases. Plot 276 includes an oxygen trend 278 and a carbon dioxide trend 280 associated with a sample breath. Vertical lines 282, 284 represent transition positions of the breath phase. The left of vertical line 284 is a first phase 286 that represents an absolute dead-space. A second phase 288 between vertical lines 282 and 284 generally occurs over a relatively short period of time with the gas concentration rapidly changing as a function of time. A third phase 290, to the right of vertical line 284, represents that area of a breath cycle wherein the concentration plateaus or only slowly increases while volume continues to accumulate. Vertical line 292, generally between vertical lines 282 and 284 delineating phase II 288 from phase I 286 and phase III 290, represents the Aitkin dead-space. The volume, that point where vertical line 292 intersects abscissa 294, represents the breath dead-space and is a combination of absolute and physiologic dead-space.

The respiratory quotient (RQ) as explained above is represented on plot 276 at line 296. RQ 296 represents the ratio of carbon dioxide volume to oxygen volume for the breath represented in plot 276. Analyzer 32 continually monitors RQ 296 with respect to the detected values of oxygen 278 and carbon dioxide 280 such that an anomaly in either of oxygen trend 278 or carbon dioxide trend 280 would be represented in a time-aligned anomaly in RQ 296. Upon the detection of an anomaly in RQ 296, analyzer 32 verifies the accuracy of oxygen value 278 and carbon dioxide value 280 to auto-correct an oxygen value or a carbon dioxide value that does not correspond to the RQ value as determined from the time aligned physiological mirror of the corresponding breath oxygen value and carbon dioxide values.

Figure 1:
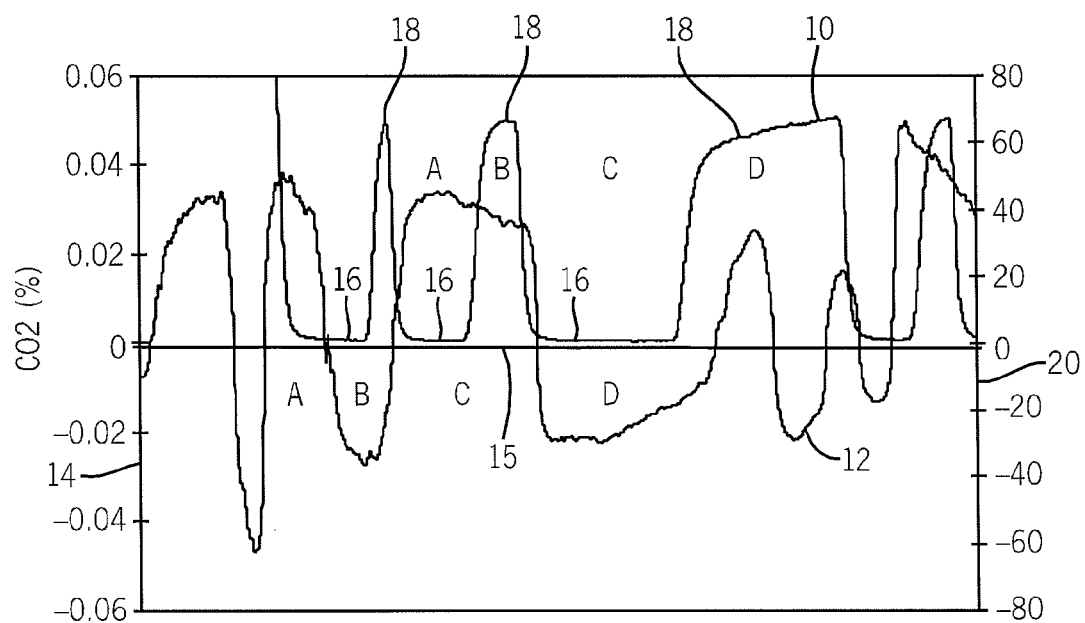
FIG. 1 is a schematic representation of data representation of prior art devices.
Figure 16:
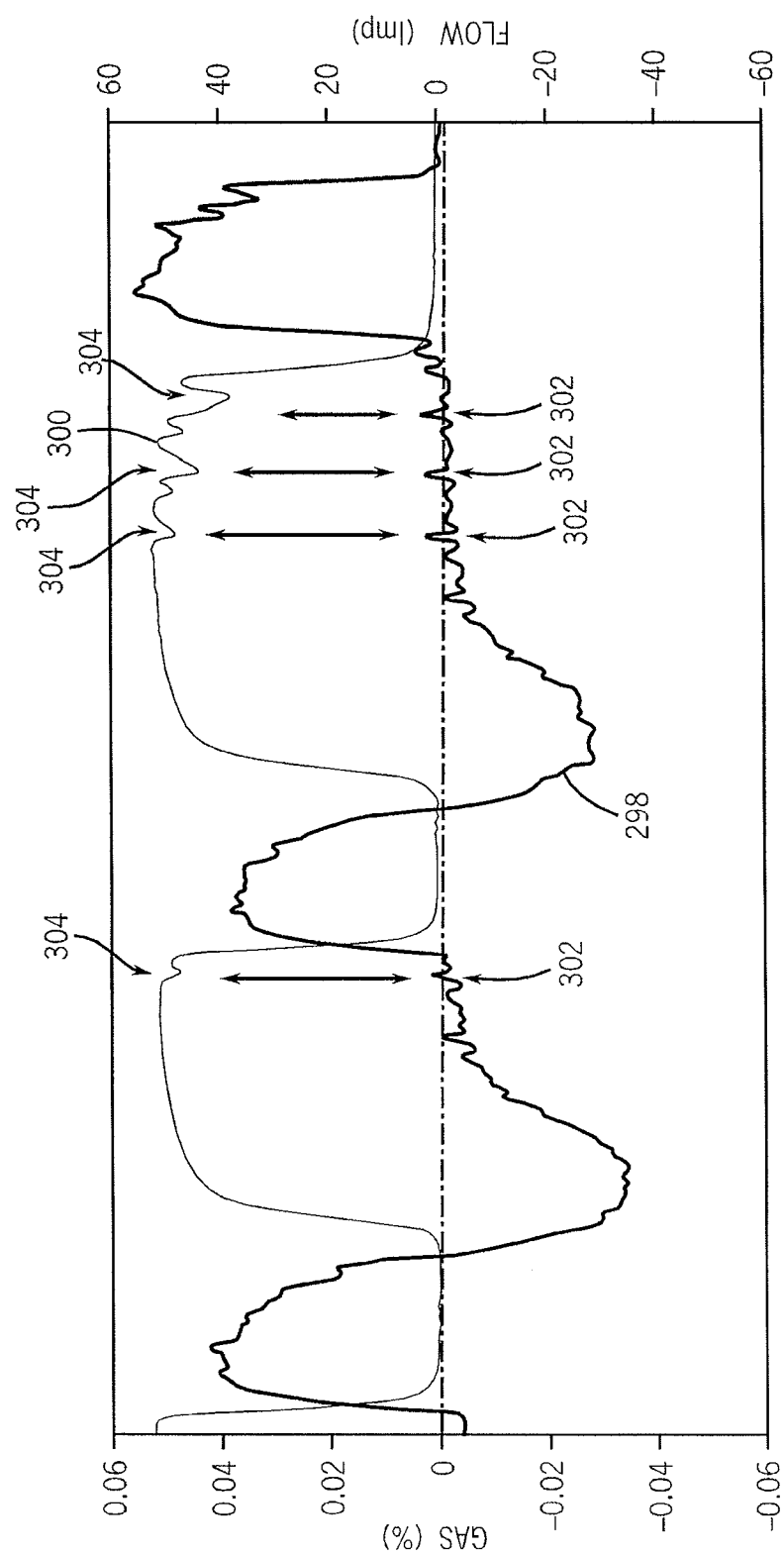
FIG. 16 is a graphical representation of a flow reversal synchrony that shows the time aligned flow and gas concentration values achieved by the respiration gas monitoring system shown in FIG. 2.

In addition to the physiological mirror, dead-space, and response time enhancements discussed above, analyzer 32 includes a flow reversal protocol as graphically represented in FIG. 16. Comparing FIGS. 1 and 16, it is shown that analyzer 32 performs a flow reversal synchronization of the trends associated with flow 298 and a gas concentration value 300. As shown in FIG. 16, pulsatile effects 302 monitored by the flow generally correspond to pulsatile effects 304 monitored in the gas value 300. Accordingly, temporally-aligning the pulsatile effects 302 in the flow 298 with the pulsatile effects 304 in the gas value 300 provides for temporal alignment of the respective trends associated with both flow and gas concentration value. As will be described further below with respect to FIG. 21, such alignment provides a well-organized and readily understandable flow and concentration output as compared to that which is generally shown in FIG. 1.

Figure 17:
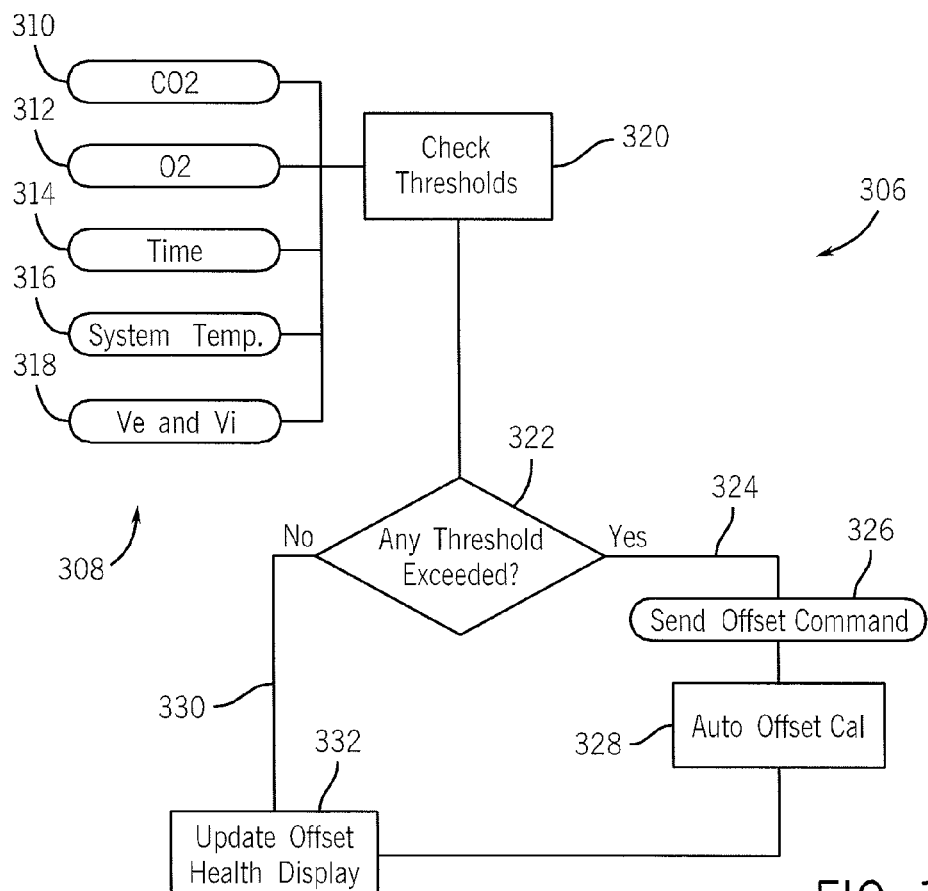
FIG. 17 is a schematic representation of a threshold calibration and check procedure performed by the respiration gas monitoring system shown in FIG. 2.

Analyzer 32 includes a number of calibration and operation procedures as shown in FIGS. 17-20. Referring to FIG. 17, analyzer 32 includes a threshold confirmation protocol 306 wherein, during operation, analyzer 32 receives a plurality of inputs 308 associated with a carbon dioxide value 310, an oxygen value 312, a time value 314, a system temperature value 316 and a signal input value 318. Understandably, other inputs could also be provided to analyzer 32. Threshold confirmation protocol 306 automatically checks to confirm that thresholds associated with any of the inputs 308 do not exceed or otherwise not satisfy desired threshold values. It is further understood that each of the thresholds associated with threshold confirmation protocol 306 can be configured by a user to a desired value. Threshold confirmation protocol 306 determines if any of the checked thresholds 320 are exceeded 322. If any of the desired thresholds are exceeded 324, protocol 306 delivers an offset command to a user 326 and/or performs an automatic offset calibration 328 as described further below. In the event that no threshold is exceeded during operation of the analyzer 32, the analyzer updates the offset health display 332 associated with the checked thresholds 330.

Figure 18:
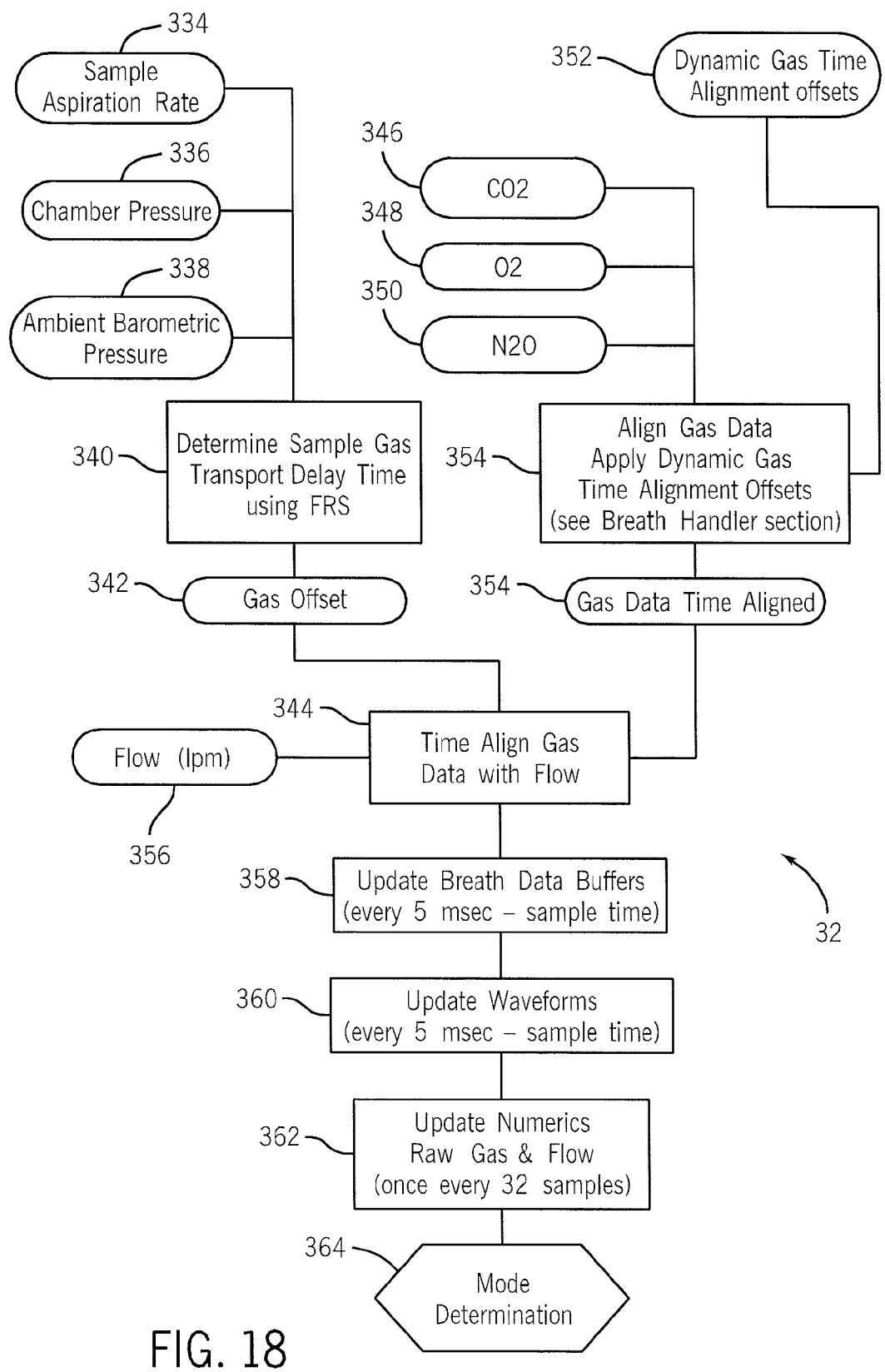
FIG. 18 is a schematic representation of an ambient condition flow and gas concentration alignment procedure performed by the respiration gas monitoring system shown in FIG. 2.

Referring to FIG. 18, analyzer 32 calculates a sample aspiration rate 334, detects an analyzer pressure 336, an atmospheric pressure 338, determines a sample gas transport delay time, and implements the flow reversal synchronology 340 as described above with respect to FIG. 16. Analyzer 32 then generates a gas value offset 342 which is utilized for time alignment of gas data with flow data 344. Analyzer 32 detects a carbon dioxide value 346, an oxygen value 348 and a nitrous oxide value 350 in conjunction with the dynamic gas time alignment offsets 352 as discussed above with respect to FIGS. 12-15, finds the gas data 354 and communicates the time aligned gas data 354 and the flow data 356 to time align the gas and flow data 344. Preferably, analyzer 32 updates the breath data buffers sample every five milliseconds 358 and updates the waveforms 360 associated with the time aligned gas and flow data 344 for every sample as well. It is appreciated that other breath data buffer update and time alignment schedules may be utilized that are more or less frequent than the preferable five millisecond and every breath sample intervals disclosed above.

Figure 19A:
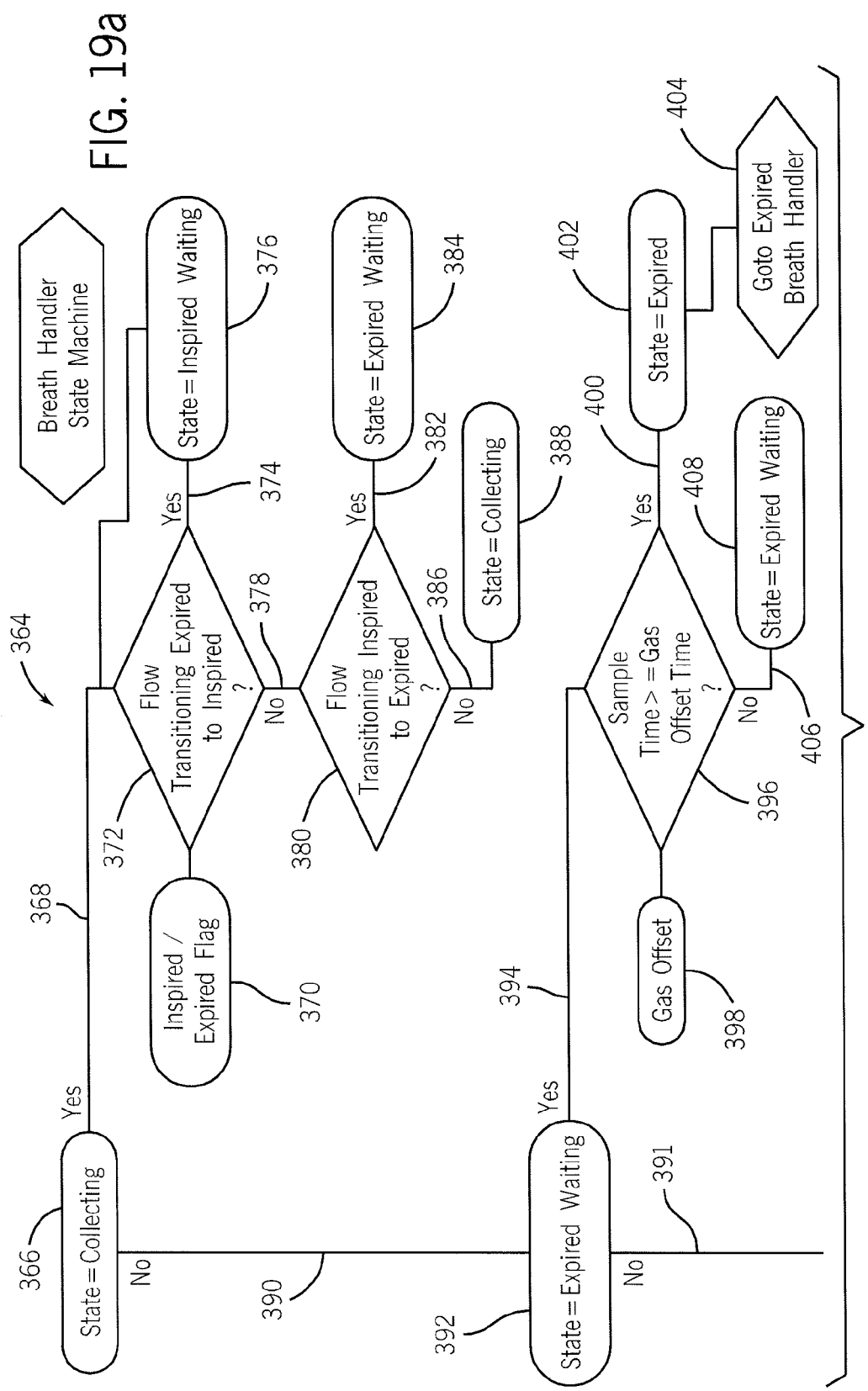
FIGS. 19a and 19b are a schematic representation of a flow cycle determination and correction procedure performed by the respiration gas monitoring system shown in FIG. 2.
Figure 19B:
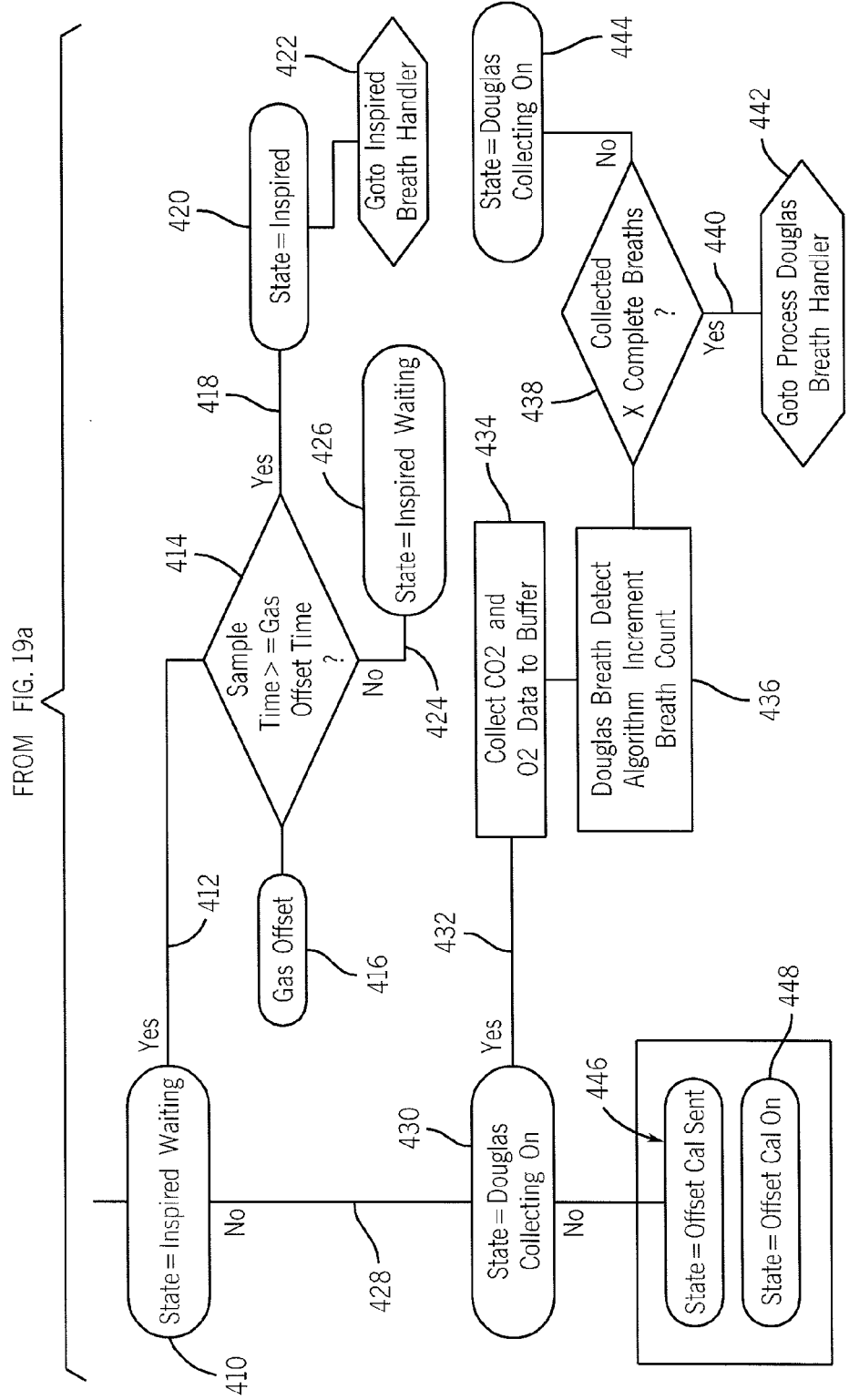

Approximately every 32 samples, analyzer 32 optionally updates the numeric associated with the raw gas and flow data 362 as a service performance monitoring function to allow background monitoring of the performance of analyzer 32. The information associated the system performance monitoring function may occur at any given interval and may be hidden from a user and accessible only in an analyzer service or monitoring window separate from the respiration data window associated with display 36. Analyzer 32 next performs a mode determination 364. As shown in FIGS. 19a and 19b, mode determination 364 includes a determination 366 as to whether the analyzer 32 is collecting data. During collection of data 368, mode determination 364 monitors an inspired/expired flag 370 to determine a flow transition from an expired to an inspired flow direction 372. If the flow is transitioning from an expired to an inspired flow direction 374, mode determination 364 provides a delay 376 to wait for an inspired value. The flow is not transitioning from an expired to an inspired flow 378, mode determination 364 determines whether flow is transitioning from inspired to an expired flow 380. If the flow is transitioning from an inspired to an expired flow 382, mode determination 364 enters an expired waiting state 384. And if the flow is not transitioning from inspired to expired flow 386, mode determination 364 confirms a collecting state 388.

Figure 20A:
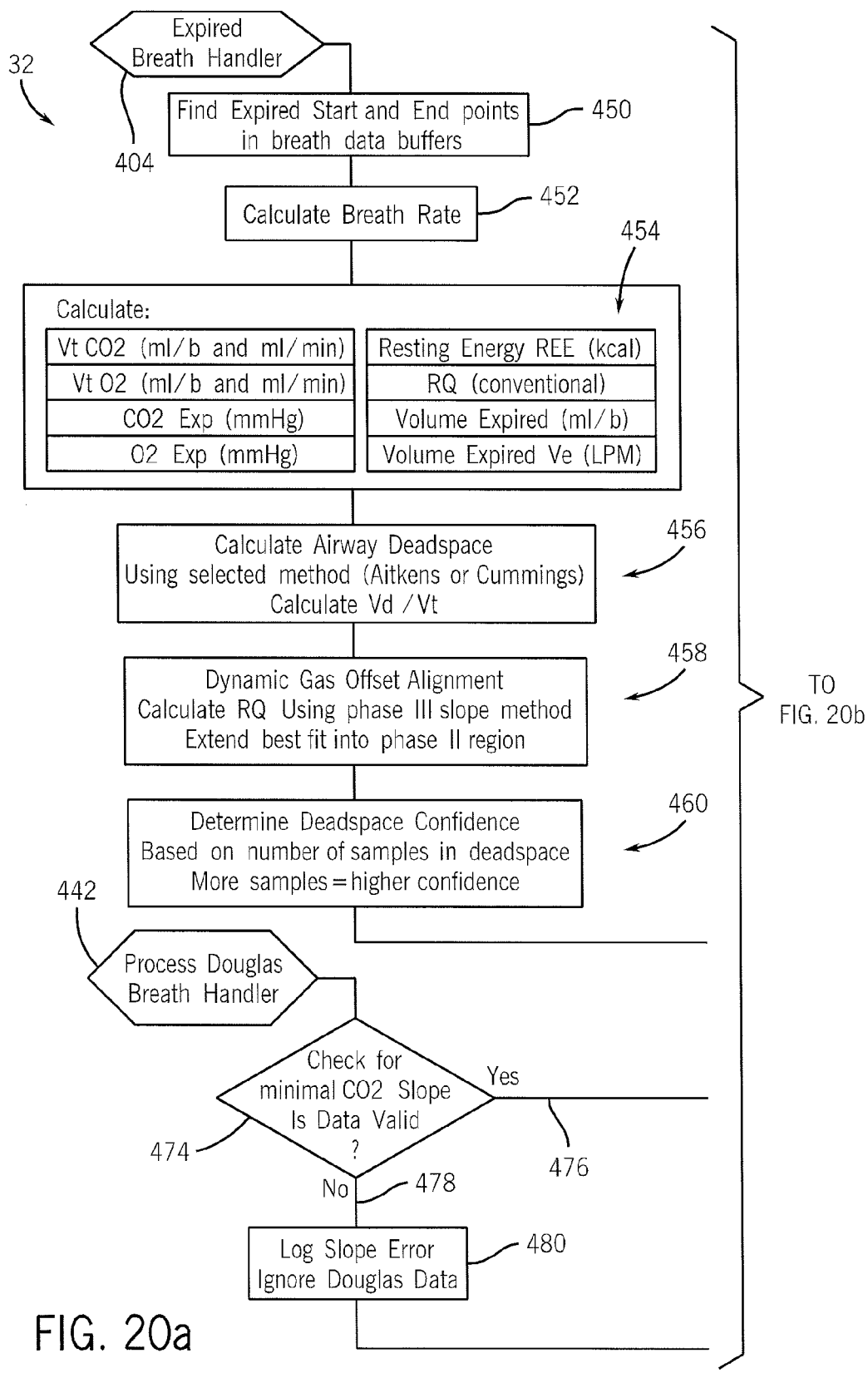
FIGS. 20a and 20b are a schematic representation of a time aligned respiration information generation procedure that accounts for the flow cycle determination and correction procedure shown in FIGS. 19a and 19b.
Figure 20B:
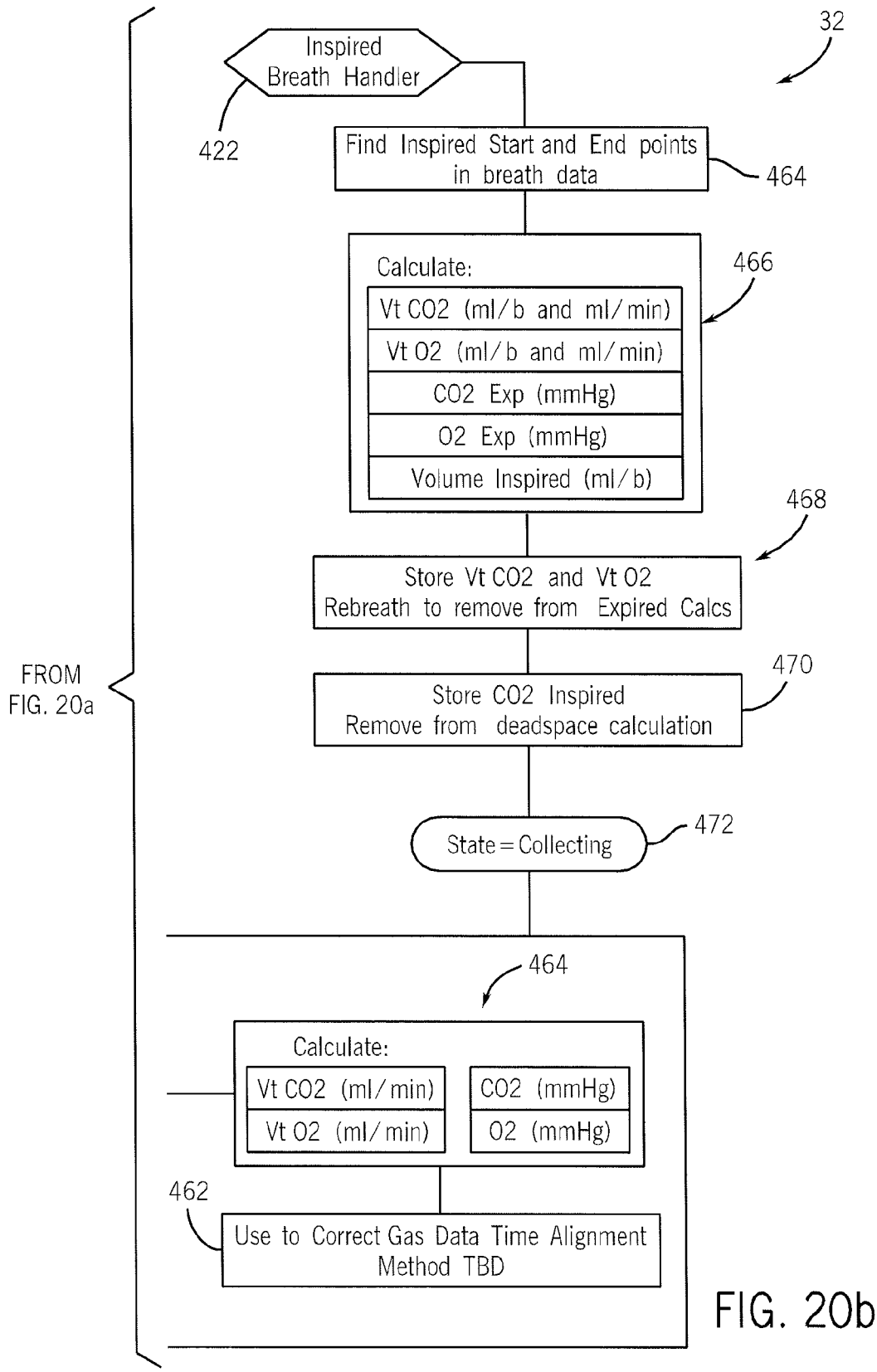

When mode determination 364 is not in a collecting state 390, mode determination 364 determines whether it is an expired waiting state 392 and, if so, 394 monitors a sample time as compared to a gas offset time 396 associated with an inputted gas offset 398. If the sample time is greater than a gas offset time 400, mode determination 364 associates the state as expired 402 and directs operation of analyzer 32 to expired breath handling 404 as shown in FIGS. 20a and 20b. When the sample time is not greater than the gas offset time 406, mode determination 364 is directed to an expired waiting 408 state. If mode determination 364 is not in a collecting state 390 and is not in an expired waiting state 392, mode determination 364 determines an inspired waiting state 410. And if the mode determination 364 is in an inspired waiting state 410, 412, mode determination 364 determines whether a sample time is greater than or equal to a gas offset time 414 as determined by gas offset 416. The sample time is greater than the gas offset time 418, mode determination 364 confirms an inspired state 420 and directs operation of analyzer 32 to inspired breath handling 422 mode as shown in FIG. 20b. If the sample time is not greater than or equal to the gas offset time 424, mode determination 364 maintains an inspired waiting state 426.

If analyzer 32 is not in a collecting state 390, not in an expired waiting state 391, and not in an inspired waiting state 428, mode determination 364 automatically checks a Douglas collecting state 430. When analyzer 32 detects the connection to a Douglas bag collecting system 432, analyzer 32 collects gas from the Douglas bag 434 and performs a Douglas breath detect algorithm and increment breath count 436 to mimic a breath cycle when analyzer 32 is connected to a Douglas bag. When Douglas collecting state 430 is activated, analyzer 32 determines whether a desired number of breaths have been collected 438 and, if so, 440 directs mode determination 364 to Douglas bag breath handling 442 as shown in FIG. 20a. Analyzer 32 maintains Douglas collecting state 430, 444 until a desired number of breaths have been collected. Upon confirmation of a no collection mode determination 364, analyzer 32 further includes a number of offset calibration options 446, 448 utilized to not process breath data during offset calibration of analyzer 32. Such a configuration allows analyzer 32 to be configured for operation with offset calibrations as may be required by any particular patient.

FIGS. 20a and 20b show the initialization calibration procedure associated with expired breath handling 404, inspired breath handling 422 and Douglas bag breath handling 442. When analyzer 32 begins in expired breath handling 404, analyzer 32 determines expiration start and end points associated with the breath data buffers 450. Analyzer 32 determines a breath rate 452 and calculates a plurality of parameters associated with an acquired sample value 454. Analyzer 32 then calculates the sample values 454, patient or respiration path dead-space 456, and dynamically aligns the gas offset 458 using the calculated RQ and the calculated dead-space 456. During expired breath handling 404, analyzer 32 determines a dead-space confidence 460 determined by a number of dead-space values for each associated sample. Having adjusted for dead-space variations, expired breath handling 404 corrects gas data with time alignment 462 utilizing any of the methods discussed hereabove and then calculates 464 volumes and pressures associated with the constituents of the sample acquired.

Comparatively, inspired breath handling 422 determines an inspired start and end points in breath data of the sample acquired, calculates 464 the volume and pressure of the constituents of the acquired sample 466, stores the calculated values and performs a rebreathe operation to remove previously acquired calculations 468. Inspired breath handling 422 stores an inspired carbon dioxide value 470 and adjusts the inspired carbon dioxide value from the dead-space calculation as previously described with respect to FIG. 15. Inspired breath handling 422 confirms a collecting state 472 and proceeds to correct gas data time alignment 462 and calculations 464.

During Douglas bag breath handling 442, analyzer 32 performs a minimal carbon dioxide slope check 474 and if the acquired carbon dioxide value is valid 476, Douglas bag breath handling 442 proceeds to calculations 464. If the carbon dioxide slope data check 474 is invalid or below a desired threshold 478, Douglas bag breath handling 442 maintains slope error data and disregards the determined Douglas bag data in proceeding to the correct gas data time alignment 462 and calculation 464. Accordingly, regardless of where in a respiration cycle analyzer 32 begins data acquisition, analyzer 32 auto-corrects for various parameters that can be acquired during any given phase of the respiration cycle.

As previously mentioned, collecting a patient's expired gases allows analyzer 32 to perform time-independent analysis of a gas source. When connected to a Douglas bag and a sensor 34, analyzer 32 periodically switches from measuring the patient to measuring the gases from a collection vessel for a brief time, thereby performing a time independent RQ determination. Any error between the instantaneously calculated or real-time RQ value and the Douglas Bag RQ value can be used to make finer adjustment to the instantaneously calculated RQ value. The collection vessel can simply be connected to the exit port of a ventilator, connected directly to a patient flow thereby circumventing any ventilator mixing, or other adequately purged collection vessels. It is further envisioned that analyzer 32 be configured to automatically acquire the Douglas bag sample thereby eliminating any clinician intervention and rendering very accurate trend Douglas bag RQ data.

Still referring to FIGS. 20a and 20b, analyzer 32 further includes several breath alignment correction procedures and calibration procedures. A first breath alignment correction is a flow aspiration correction procedure. A sample gas flow being aspirated from the flow path of sensor 34 is calculated by analyzer 32 and the corresponding breath parameters are adjusted for the sensor aspirated gas values. The sensor aspirated gas causes an error in the patient flow measurement that must be corrected. Since the location of the sensor 34 gas sampling tube 48 (shown in FIG. 6) is between the tubes 44, 46 (also shown in FIG. 6) used for the flow measurement, the error is asymmetric and opposite in direction depending on whether the patient flow is an inhalation or an exhalation and is a function of the magnitude of the patient respiration flow. If the gas were removed further down stream after the flow ports, this correction to the flow measurement would not be necessary, but an additional time domain shift would be required. In either case, if the patient flow is not significantly greater than the aspiration flow, such as in the case of monitoring small infants, entrainment will occur which must also be addressed.

In the case where the gas is being aspirated between the flow measurement ports, the gas being aspirated produces a pressure drop that is unequal across the ports and is direction dependent that appears as patient flow. Also, the flow error, while proportional to the aspiration rate, is not the same as the aspiration rate. For example, if one is aspirating at 200 ml/min (0.2 lpm), simply adding 0.2 lpm back into the patient flow reading does not adequately reflect the required correction. The error, however, is proportional to the aspiration rate as well as the patient flow rate, and changes with patient flow direction. Analyzer 32 empirically determines the magnitude and direction of the necessary corrections needed to correct the flow readings for this sensor aspiration.

As the patient flow becomes small or approaches zero, the aspiration flow becomes more significant and a condition known as entrainment occurs. Here, the amplitude of the gas signals becomes diluted with other gasses. For example, if the patient gasses are being expired at a low flow rate compared with the aspiration rate, a portion of the sample being aspirated may be redirected into the analyzer. The measured patient flow and controlled and measured aspiration flow is used to determine the true concentration of the patient gas as communicated to the gas sensors. This type of flow correction generally only needs to be performed on infant and premature infant flow levels, as the transitions such pediatric breathing occurs too quickly to be determined by a digitizing sample rate of preferably 5 msec per sample acquisition.

Analyzer 32 includes a dead-space confidence qualifier procedure that is generally applicable with very high breath rates and low dead-space quantities, such as with infants, wherein the total time involved in measuring the dead-space is very short. In such a situation, the time from the flow crossing or start of expiration until the phase II 288 dead-space point 284 may be so short that the insufficient data samples are acquired. If very few data samples are captured during this time, the dead-space confidence qualifier provides feedback to the technician as to the level of confidence in the result. The confidence is based on how many samples, approximately 1 sample every 5 milliseconds, are captured within the dead-space time as calculated using the Aitkin method as shown in FIG. 15. Indicator colors such as green for a high or good level of confidence, yellow for caution, and red for warning may be utilized in display 36 as described below with respect to FIG. 21. It is envisioned that greater than 10 samples would produce a high or good level of confidence, 3 to 10 samples would warrant a caution, and less than 3 samples should produce a warning as to the quality of the dead-space qualifier. The color is used for either the display of the dead-space qualifier itself or as the background color highlighting the dead-space numerical display.

Analyzer 32 also includes a flow offset drift compensation procedure. Analyzer 32 monitors patient respiration flow using a differential pressure transducer connected to sensor 34. The pressure transducer is generally sensitive to changes in temperature. A standard pressure/temperature calibration is performed which characterizes the transducer. In addition, a flow offset drift compensation is performed in an attempt to minimize the zero (offset) error due to changes in temperature between offset calibrations. The method used characterizes pressure vs. temperature using a second order polynomial. Using this equation, a prediction is made of what the pressure would be as temperature changes for the "zero" pressure from the zero pressure determined at the last offset calibration. The flow offset drift compensation procedure acquires an offset calibration temperature TO and acquires a second temperature TX during acquisition of the flow sample. Analyzer 32 calculates pressures P0 and PX using TO and TX and then calculates an offset pressure, Poffset, as the difference between P0 and PX. Analyzer 32 subtracts Poffset from the sampled pressure prior to calculating patient flow thereby correcting for flow offset drift.

Analyzer 32 is also configured for automatic calibration of operation of the analyzer 32 and sensors 62, 64, 66. Preferably, sensors 62, 64, 66 are chosen to be inherently gain stable. The gain stability is due to the fact that the sensors have a high degree of resolution at the lower end of their measurement range and lesser resolution towards the upper end. This is desirable since most of the time measurements will be made in the lower part of the range of the respective sensors 62, 64, 66. Understandably, with higher resolution, sensor drift becomes more apparent. The present invention communicates atmospheric air through housing 58 of analyzer 32 to correct for offset drift automatically using an inexpensive calibration gas, i.e. room air.

The room air communicated through housing 58 is utilized as an inhalation sample and a mixed gas having a known composition and or respiratory quotient is communicated to analyzer 32 to provide an exhalation sample. The ambient oxygen concentration is calculated by correcting the ambient oxygen value measured by oxygen sensor 62 for ambient water vapor dilution through utilization of the information detected by temperature and humidity sensors 78, 80 shown in FIG. 3. The room air is also passed through a carbon dioxide scrubber to insure a zero carbon dioxide value. The concentration of the known gas is entered by an operator. Preferably, the concentration of the constituents of the mixed gas is selected such that a result respiratory quotient is within a normal physiological range. One of valves 72, 74, 76, 89, or an additional valve, and pump 70, or another supplemental pump, cooperate to switch the source of gas communicated to sensors 62, 64, 66 between the mixed gas and the room air.

Preferably the mixed gas is provided at a flow rate that is greater than a sample aspiration rate with the excess gas being vented. A pneumatic venturi device is connected between analyzer 32 and the inlet of the mixed gas and creates a pressure differential perceived by flow sensor 67. According, analyzer 32 mimics a breath cycle with real-time operation feedback and detectable gas transitions. It is further understood that, by aligning the artificially developed flow indication with a measured patient flow level, the operability of flow sensor 67 can be confirmed as well as providing a confirmation that the flow of mixed gas is accurately detected by flow sensor 67.

User selectable triggers perform offset calibrations of sensors 62, 64, 66 that include time from last calibration, temperature from last calibration, carbon dioxide inspired level, oxygen inspired level, and tidal volume imbalance (Ve/Vi) over a series of sample breaths. The tidal volume imbalance provides a parameter that is particularly useful for determining offset calibration. Determined over a reasonable period of breaths (for example, a 7 breath rolling buffer), the total inspired breath volume should correlate to the total expired breath volume. If the values do not correlate, the discrepancy provides indicia that analyzer 32 flow offset has drifted, or that a leak is present in the gas circuit. Also, as part of this feature, the display 36 includes a health meter indication for each trigger.

As shown in FIG. 3, flow leak valve 89 of analyzer 32 is configured to allow analyzer 32 to check for leaks in the gas sampling path and those in the patient flow measurement path. The gas sampling path is from the sensor 34 to the input 57, 59 as shown in FIG. 1. If a leak exists in the gas sampling path and is small, gas waveforms will still be present but will show up with a larger time lag from the patient flow signal. This will result in greater dead-space readings than what are actually present. If the leak in the sampling path is larger, the dead-space becomes very large and the system experiences difficulty attempting to align the gas concentration with flow and presents a detectable error condition.

To detect small gas sampling leaks, valve 89 is used to close off the sampling line internal to the system immediately after the input to the housing. When closed, the sample pump is used to draw a vacuum to a lower pressure. When this pressure is reached, the pump is turned off and this pressure must be maintained for a desired time. If internal leaks are present, the lower pressure will quickly climb back to ambient pressure providing an indication of an internal leak condition. External leaks are detected as a flow error if either of tubes 44, 46 have a leak. The noticeable affect is an imbalance between inspired and expired volumes depending on location. During a leak check, a user is instructed to connect plugs to a flow sensor and analyzer 32 shuts off valve 72 to either input 57, 59 uses pump 70 to apply positive pressure to the system. As above, positive pressure above ambient must be maintained for a period of time to indicate a no-leak condition.

Analyzer 32 is further configured to automatically calibrate operation of sensors 62, 64, 66 for variable environmental factors including ambient gas concentrations and ambient temperature and humidity. 11. Preferably, oxygen sensor 64 is an electrochemical device. Although such devices generally include an electrical or mechanical temperature compensation feature, such corrections are insufficient to address the parameters associated with respiration monitoring. That is, such corrective measures introduce errors of inherent to the corrective devices. Accordingly, analyzer 32 is constructed to operate in such a way as to address the inherent errors associated with operation of the sensor. Analyzer 32 also adjusts operation as a function of humidity variations associated with operation of the sensors 62, 64, 66.

Figure 21:
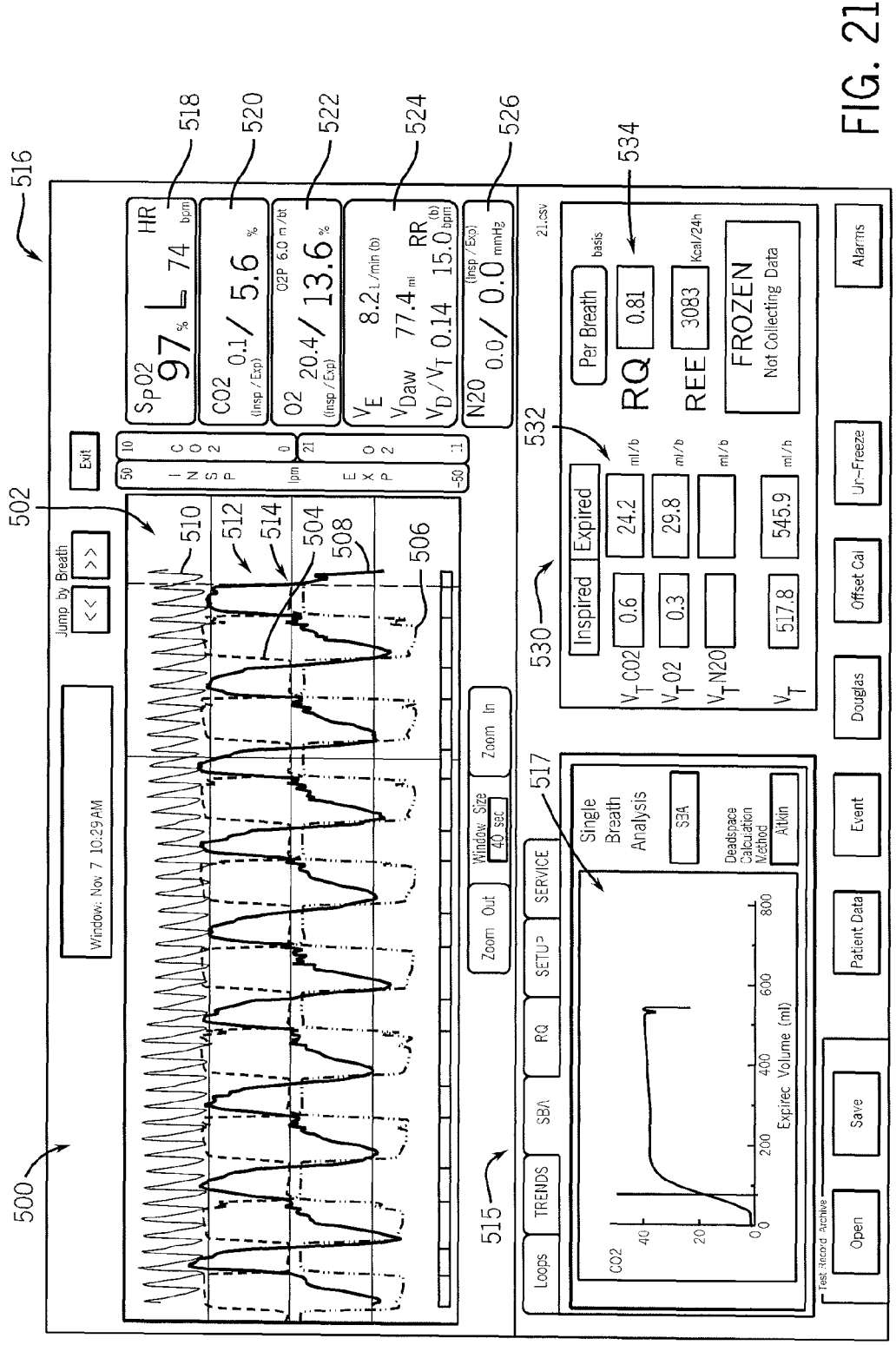
FIG. 21 is an exemplary display of the information acquired and corrected by the respiration gas monitoring system shown in FIG. 2.

FIG. 21 shows an exemplary time-aligned respiration output 500 generated by analyzer 32. Output 500 includes a trend window 502 configured to display a carbon dioxide concentration 504, an oxygen concentration 506, a flow value 508, and a saturated blood oxygen value 510 in a common screen 512 on a common plot 514. As discussed above, each of the respiration cycle concentration values 504, 506, 508, 510 are temporally aligned along the data trend. The carbon dioxide concentration 504 and the oxygen concentration 506 values are generally produced as mirror images of one another such that quick viewing and interpretation of the breath data is achieved. It is further appreciated that the oxygen concentration data could be acquired by scaling the respiration data by a factor such that it correlates to the carbon dioxide concentration value. Alternatively, it is understand that analyzer 32 be configured to monitor the oxygen content deficiency and that this value then be inverted to generally mimic the carbon dioxide concentration value. Both configurations provide a carbon dioxide and oxygen concentration displayed value generally similar to that shown in FIG. 21.

It will further be appreciated that the respiration flow value 508 is also time aligned with the carbon dioxide and oxygen concentrations 504, 506. Output 500 also includes a dead-space trend display 515 configured to allow viewing of both the common plot 514 and a dead-space trace 517 that is utilized to calibrate and align the common trends of the common plot 514. A plurality of value displays 516 are included in output 500 and provide exact values of any of the oxygen saturation value 518, a carbon dioxide concentration 520, an oxygen concentration 522, a flow data 524, and nitrous oxide concentration 526 associated with the data related with any given time along common plot 514. During operation of analyzer 32, any given time of acquisition along common plot 514 can be interrogated for the data associated therewith.

Output 500 also includes a volume and RQ display window 530 configured to display rolling tidal volume data 532 associated with inspired and expired volumes as well as rolling RQ data 534. Analyzer 32 is configured to acquire and determine the oxygen concentration, carbon dioxide concentration, and nitrous oxide concentration on a breath-by-breath basis. Analyzer 32 temporally aligns that acquired data and display and corrects the data as it is acquired. The compact and time aligned display of the data at output 500 provides a system wherein a technician can quickly ascertain the respiration performance of a patient as well as performance of the analyzer. Understandably, output 500 could be configured to allow various levels of operator interaction with the operation and performance of analyzer 32 as well as the various levels of data, calculation, modification, and calibration performed thereby. Accordingly, analyzer 32 is highly versatile, easy to operate, simple to configure for desired operation, and provides an output that allows for quick diagnosis and analysis of patient condition.

Therefore, one embodiment of the invention includes a side-stream respiration monitoring system having a flow sensor and a controller. The flow sensor is constructed to be disposed in a respiration flow path to detect various parameters of the respiration flow. The controller is connected to the flow sensor and is configured to determine a respiration flow value and at least a portion of a composition of the flow. The controller temporally associates the respiration flow value and the portion of the composition on an approximately breath-by-breath basis to provide real-time breath-by-breath respiration monitoring.

Another embodiment of the invention includes a respiration monitoring system that has a flow sensor, an analyzer, and a controller. The sensor is constructed to detect a respiration flow and acquire a side-stream sample of the flow. The analyzer is constructed to determine an amount of a gas carried on the respiration flow and the controller is configured to automatically calibrate the analyzer.

A side-flow respiration monitoring system according to another embodiment includes a sensor for detecting a respiration flow and acquiring a sample of the respiration flow. A monitor is connected to the sensor for determining an amount of oxygen and an amount of carbon dioxide in the respiration flow on a breath-by-breath basis. A display is connected to the monitor for displaying information associated with the amount of oxygen and carbon dioxide on a common plot to provide comprehensive time-aligned respiration information.

A further embodiment of the invention is a method of monitoring respiration information that includes measuring a patient flow and a patient pressure and acquiring a side-stream breath sample. The method determines a flow of the side-stream breath sample and a concentration of oxygen and a concentration carbon dioxide in the acquired side-stream breath sample. The determined flow and concentrations are temporally aligned on approximately a breath-by-breath basis.

In another embodiment, a breath-by-breath analyzer includes a sensor constructed to engage a respiration flow. The analyzer is connected to the sensor and is configured to determine a pressure and at least a portion of a composition of the respiration flow. The analyzer includes an adapter that is configured to engage the sensor such that a first portion of the respiration flow passes through the sensor and a second portion of the respiration flow passes through the adapter. Such a construction provides a high-flow analyzer that is configured to monitor respiration performance on a breath-by-breath basis.

Yet another embodiment includes a respiration monitoring system having an oxygen sensor constructed to detect an oxygen concentration and a carbon dioxide sensor constructed to detect a carbon dioxide concentration. The monitoring system includes first and second inputs wherein each input is constructed to fluidly connect a respective gas source to the oxygen and carbon dioxide sensors.

A respiration monitoring device according to another embodiment includes at least one valve, a pump connected to the valve, an oxygen sensor, a carbon dioxide sensor, and a control. The control is configured to control operation of the valve and pump for communicating a gas to each of the oxygen sensor and the carbon dioxide sensor to mimic a breath flow and a breath composition.

Another embodiment includes a physiologic monitor controller having an input configured to receive a physiologic signal and a correction protocol configured to determine an output by adjusting a value of the input in an amplitude domain and a time domain.

It is further understood that specific details described above are not to be interpreted as limiting the scope of the invention, but are provided merely as a basis for teaching one skilled in the art to variously practice the present invention in any appropriate manner. Changes may be made in the details of the various methods and features described herein, without departing from the spirit of the invention

What is claimed is:

1. A side-stream respiration monitoring system comprising:
    a flow sensor constructed to be disposed in a respiration flow path; and
    a controller connected to the flow sensor and configured to
        1) determine a respiration flow value through the respiration flow path and at least a portion of a composition of the respiration flow on a breath-by-breath basis that includes pulsatile effect respiration data; and
        2) temporally associate in a time-domain each of the determined respiration flow value and the determined portion of the composition to account for at least two of flow path resistances, dead-space volumes, and flow composition for approximately each breath.

2. The system of claim 1 wherein the portion of the composition includes at least one of a concentration of oxygen and a concentration of carbon dioxide.

3. The system of claim 2 wherein the concentration of oxygen and the concentration of carbon dioxide is determined for each inspiration and expiration.

4. The system of claim 1 wherein the respiration flow value is pressure based.

5. The system of claim 1 wherein the controller further comprises an analyzer connected to the controller and configured to automatically adjust operation of the controller in response to ambient conditions.

6. The system of claim 5 wherein the analyzer includes a carbon dioxide sensor that is stable for gain and an oxygen sensor that is stable for offset.

7. The system of claim 1 further comprising a display configured to output the temporally associated respiration flow value and the portion of the composition on a common ordinate and abscissa.

8. The system of claim 7 wherein the controller offsets an ordinate scale of an oxygen value by an inspired oxygen value such that the output of the oxygen value is generally a mirror image of a carbon dioxide value.

9. The system of claim 7 wherein the controller calculates and inverses an oxygen deficit from the composition of the flow such that the output of the oxygen value is generally a mirror image of a carbon dioxide value.

10. The system of claim 1 wherein the controller includes a first input for fluidly connecting with the sensor and a second input for fluidly connecting the controller to a gas source.

11. The system of claim 10 wherein the gas source is one of another flow sensor, a Douglas gas, and a gas bottle.

12. The system of claim 1 further comprising a physiological detector connected to the controller for receiving a physiological signal, the controller configured to temporally associate physiological signal with the respiration flow value and the portion of the composition.

13. The system of claim 12 wherein the physiological detector is a heart beat monitor.

14. The system of claim 1 further comprising an adapter for engaging the flow sensor and configured to allow a first portion of a respiration flow to bypass the flow sensor so that the first portion of the respiration flow is a multiple of the flow through the flow sensor.

15. A respiration monitoring system comprising:
a flow sensor constructed to detect a respiration flow and acquire a side-stream sample of the flow;
an analyzer constructed to determine an amount of a gas carried on the respiration flow; and
a controller configured to automatically calibrate the analyzer to address a first deviation of a first sensor and address a second deviation that is different than the first deviation for a second sensor.

16. The system of claim 15 wherein the gas includes any gas from the group of carbon dioxide, oxygen, and nitrous oxide.

17. The system of claim 15 wherein the controller is configured to monitor an ambient condition and adjust operation of the analyzer in response to the ambient condition.

18. The system of claim 17 wherein the ambient condition is at least one of ambient oxygen content, ambient carbon dioxide content, ambient nitrous oxide content, ambient temperature, ambient air humidity, and barometric pressure.

19. The system of claim 15 wherein the controller is configured to repeat a calibration process periodically without interrupting operation of the system.

20. The system of claim 15 wherein the analyzer is configured to monitor oxygen and carbon dioxide levels in the side-stream flow and the controller is configured to associate the amount of oxygen and carbon dioxide to a volume of the respiration flow.

21. The system of claim 15 further comprising a housing constructed to enclose the controller and the analyzer and having the flow sensor fluidly connected therethrough and a display connectable to the housing.

22. The system of claim 15 wherein the controller is configured to adjust for dead-space associated with an aspiration flow path.

23. The system of claim 15 wherein the system is configured to be hand carried.

24. A side-flow respiration monitoring system comprising:
a sensor for detecting a respiration flow and acquiring a sample of the respiration flow;
a monitor connected to the sensor for determining an amount of oxygen and an amount of carbon dioxide in the respiration flow on approximately a breath-by-breath basis wherein the monitor is constructed to adjust the determined amounts of oxygen and carbon dioxide for a dead-space associated with an aspiration path; and
a display connected to the monitor for displaying information associated with the amount of oxygen and carbon dioxide on a common plot.

25. The system of claim 24 wherein the monitor is configured to determine a respiration flow value from a pressure differential detected by the sensor.

26. The system of claim 24 wherein the monitor includes an oxygen sensor, a pressure sensor, and a carbon dioxide sensor.

27. The system of claim 24 further comprising a detector attached to the monitor to acquire a heart rate signal, the monitor configured to align the heart rate signal, the respiration flow, amount of oxygen, and amount of carbon dioxide.

28. The system of claim 24 further comprising an adapter for connecting to the sensor for reducing a flow pressure by a multiple of a flow pressure of the sensor.

29. The system of claim 24 wherein the monitor is constructed to determine an ambient condition and adjust the displayed information in response to the ambient condition.

30. The system of claim 29 further comprising a timer configured to instruct the monitor to periodically determine the ambient condition.

31. The system of claim 24 wherein the monitor is configured to calculate a physiologic mirror information and communicate the physiologic mirror information to the display.

32. The system of claim 24 wherein the monitor is configured to determine a respiratory quotient (RQ) from the amount of oxygen and the amount of carbon dioxide in the respiration flow and communicate the RQ to the display.

33. The system of claim 32 wherein the monitor adjusts one of the determined amount of oxygen and the determined amount of carbon dioxide by a comparison of the RQ to the other of the determined amount of oxygen and the determined amount of carbon dioxide.

34. A method of monitoring respiration information comprising the steps of:
measuring a patient flow and a patient pressure;
acquiring a side-stream breath sample;
determining a flow of the side-stream breath sample, a concentration of oxygen, and a concentration of carbon dioxide in the acquired side-stream breath sample for all the measured and acquired respiration information of the side-stream breath sample including non-diaphragmatic respiration information; and
temporally aligning in a time domain the determined flow with the determined concentrations of oxygen and carbon dioxide with respect to their occurrence in the acquired side-stream breath sample on approximately a breath-by-breath basis.

35. The method of claim 34 further comprising displaying the temporally aligned flow and concentrations of oxygen and carbon dioxide on a common plot for an acquired breath sample.

36. The method of claim 34 wherein the step of determining the flow of the side-stream breath sample further comprises adjusting for a dead-space of an aspiration flow.

37. The method of claim 34 wherein the step of determining the concentrations of oxygen and carbon dioxide in the side-stream breath sample comprises adjusting at least one of a value of the concentration of oxygen and a value of the concentration of carbon dioxide for a respective concentration oxygen and carbon dioxide present in an inspiration source.

38. The method of claim 34 further comprising acquiring a heart rate and temporally associating the heart rate and the determined flow and the determined concentration of oxygen and carbon dioxide.

39. The method of claim 34 further comprising determining and displaying a concentration of nitrous oxide present in the side-stream breath sample.

40. The method of claim 34 further comprising determining an amount of patient nitrous oxide exchange.

41. The method of claim 34 further comprising determining a respiratory quotient.

42. The method of claim 41 further comprising adjusting one of the determined concentrations of oxygen and carbon dioxide based on the respiratory quotient and the other of the determined concentrations of oxygen and carbon dioxide.

43. The method of claim 34 wherein the step of acquiring a side-stream breath sample includes monitoring a first portion of a breath flow and allowing non-monitored passage of a second portion of the breath flow wherein the second portion is a multiple of the first portion of the breath flow.

44. The method of claim 34 further comprising connecting a sensor for the acquiring step to a monitor for the determining steps to a display for outputting the temporally aligned flow and concentrations of oxygen and carbon dioxide.

45. The method of claim 34 further comprising connecting any two of a sensor, a monitor, and a display via a serial port connection, serial bus connection, an expansion port connection, a slot connection, a lumen tube, and a wireless communication interface.

46. The method of claim 34 further comprising providing a first sensor for a very small patient, a second sensor for a small patient, a third sensor for an adult patient, and a bypass adapter to engage the third sensor for elevated respiration flows.

47. A breath-by-breath analyzer comprising:
a sensor constructed to engage a respiration flow;
an analyzer connected to the sensor and configured to determine a pressure and at least a portion of a composition of the respiration flow;
an adapter configured to engage the sensor wherein a first portion of the respiration flow passes through the adapter and is directed to the sensor and a second portion of the respiration flow that travels in the same direction as the first portion of the respiration flow passes through the adapter and bypasses the sensor and the analyzer; and
wherein the second portion of the respiration flow is a multiple of the first portion of the respiration flow.

48. The analyzer of claim 47 wherein the analyzer includes an oxygen sensor and a carbon dioxide sensor and is configured to determine respective amounts of oxygen and carbon dioxide in an exhalation.

49. The analyzer of claim 48 wherein the analyzer is configured to determine a respiratory quotient from the determined amounts of oxygen and carbon dioxide.

50. The analyzer of claim 49 wherein the analyzer determines a respiratory quotient on a breath-by-breath basis.

51. The analyzer of claim 49 wherein the analyzer compares the respiratory quotient to one of the determined amounts of oxygen and carbon dioxide and adjusts the other of the determined amount of oxygen and carbon dioxide based on the comparison.

52. The analyzer of claim 49 wherein the analyzer automatically calibrates by mimicking a breath cycle.

53. The analyzer of claim 41 wherein the analyzer varies the rate of the mimicked breath cycle.

54. The analyzer of claim 49 wherein the analyzer is constructed to perform an operation verification based on the respiratory quotient on a breath-by-breath basis.

55. The analyzer of claim 47 further comprising a nitrous oxide sensor configured to determine an amount of nitrous oxide in a breath.

56. The analyzer of claim 47 further comprising a cardiac detector and a display, the analyzer configured to generate real-time aligned data associated with the respiration flow and the cardiac detector to generate an output on the display.

57. The analyzer of claim 47 wherein the analyzer is configured to monitor an ambient condition and adjust data associated with the portion of the composition of the respiration flow to account for the ambient condition.

58. The analyzer of claim 47 further comprising a container constructed to retain an exhalation for analysis after the exhalation and the analyzer includes a first input for connecting to the sensor and another input for fluidly connecting to the container.

59. The analyzer of claim 58 wherein the container is constructed to receive a gas having a known respiratory quotient and the analyzer is constructed to autocalibrate at least one of an oxygen sensor and a carbon dioxide sensor at least in part based on the known respiratory quotient.

60. A respiration monitoring system comprising:
an oxygen sensor constructed to detect an oxygen concentration;
a carbon dioxide sensor constructed to detect a carbon dioxide concentration;
a first input constructed to fluidly connect a first source of a breathable gas mixture to the oxygen and carbon dioxide sensors; and
a second input that is fluidly isolated from the first input and is constructed to fluidly connect a second source of a breathable gas mixture to the oxygen and carbon dioxide sensors.

61. The system of claim 60 further comprising a sensor connected to the first input and the first gas source is a patient respiration through the sensor.

62. The system of claim 61 wherein the second gas source is one of another patient respiration through another sensor, a Douglas bag, a container having a known mixture of gas, and an oxygen source.

63. The system of claim 62 wherein the container has a gas with a known respiratory quotient (RQ) and the monitoring system calculates an RQ and performs a performance check of one of the oxygen sensor and the carbon dioxide sensor based on the calculated RQ.

64. The system of claim 63 wherein the monitoring system adjusts operation of one of the oxygen sensor and the carbon dioxide sensor based on the performance check.

65. A respiration monitoring device comprising:
at least one valve;
a pump connected to the valve;
an oxygen sensor and a carbon dioxide sensor; and
a control configured to control operation of the valve and the pump for communicating a gas to each of the oxygen sensor and the carbon dioxide sensor to mimic a breath flow and a breath composition.

66. The device of claim 65 further comprising a housing configured to enclose the valve, the pump, and the control.

67. The device of claim 65 wherein the gas is provided from at least one of a Douglas bag and a gas cylinder.

68. The device of claim 65 wherein the control is configured to calculate an RQ value from a first signal generated by the oxygen sensor and a second signal generated by the carbon dioxide sensor.

69. The device of claim 68 wherein the control is configured to modify one of a value calculated from the first signal and a value calculated from the second signal based on a comparison of the RQ value and the other of the value calculated from the first signal and the value calculated from the second signal.

70. The device of claim 65 further comprising a first input constructed to fluidly connect a first gas source to the valve and a second input to fluidly connect a second gas source to the valve.

71. A physiologic monitor controller comprising:
an input configured to receive a physiologic signal; and
a correction protocol configured to determine an output by adjusting a value of the input in an amplitude domain and a time domain.

72. The controller of claim 71 wherein the amplitude domain is at least one of concentration, temperature, pressure, and flow.

73. The controller of claim 72 wherein the concentration is at least one of oxygen concentration, carbon dioxide, nitrous oxide, and water vapor concentration.

74. The controller of claim 71 wherein the correction protocol is determined in part by a type of sensor.

75. The controller of claim 74 wherein the type of sensor is a galvanic-type oxygen sensor and the correction protocol performs a first correction on a response time characteristic and second correction different than the first correction on another response time characteristic.

76. The controller of claim 75 wherein the response time characteristic is different than the another response time characteristic.

* * * * *